(12) United States Patent
Chen et al.

(10) Patent No.: US 10,736,998 B2
(45) Date of Patent: *Aug. 11, 2020

(54) KITS FOR LOCAL DELIVERY OF WATER SOLUBLE AGENTS AND METHODS OF USE

(71) Applicant: Medtronic, Inc., Minneapolis, MN (US)

(72) Inventors: Xiangji Chen, Plymouth, MN (US); Satish Pulapura, Bridgewater, NJ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/407,857

(22) Filed: May 9, 2019

(65) Prior Publication Data
US 2019/0262510 A1    Aug. 29, 2019

Related U.S. Application Data

(63) Continuation of application No. 15/963,227, filed on Apr. 26, 2018, now Pat. No. 10,314,951, which is a
(Continued)

(51) Int. Cl.
*A61L 31/16* (2006.01)
*A61L 27/14* (2006.01)
(Continued)

(52) U.S. Cl.
CPC .............. *A61L 31/16* (2013.01); *A61J 1/00* (2013.01); *A61L 27/14* (2013.01); *A61L 27/54* (2013.01); *A61L 31/06* (2013.01); *A61L 2300/418* (2013.01); *A61L 2400/04* (2013.01); *A61N 1/375* (2013.01); *A61N 1/37512* (2017.08)

(58) Field of Classification Search
CPC .......... A61L 31/16; A61L 27/14; A61L 27/54; A61L 31/06; A61L 2300/418; A61L 2400/04; A61J 1/00; A61N 1/375; A61N 1/37512

See application file for complete search history.

(56) References Cited

U.S. PATENT DOCUMENTS

2008/0128315 A1    6/2008  Buevich et al.

FOREIGN PATENT DOCUMENTS

| CN | 104490762 A | | 4/2015 | |
|---|---|---|---|---|
| WO | WO201002435 | * | 1/2010 | ............. A61L 15/42 |

OTHER PUBLICATIONS

Chia Pow-Li et al: "Use of oxidized regenerated cellulose to prevent pocket hematomas after cardiac electronic device implantation in patients on anticoagulants or dual antiplatelet therapy", International Journal of Cardiology, vol. 168, No. 4 , pp. 4406-4407, XP028757093, ISSN: 0167-5273, DOI: 10.1016/J.IJCARD.2013.05.037.

(Continued)

*Primary Examiner* — Trevor Love
(74) *Attorney, Agent, or Firm* — Sorell, Lenna & Schmidt, LLP

(57) ABSTRACT

A kit includes a mesh substrate and a polymer that is fixed to the mesh substrate. The polymer includes an active agent that is configured to elute over time. The kit further includes a hemostatic agent. The hemostatic agent is separate from the mesh substrate and the polymer. Systems and methods are disclosed.

19 Claims, 5 Drawing Sheets

Related U.S. Application Data continuation of application No. 15/913,384, filed on Mar. 6, 2018, now Pat. No. 10,034,969, which is a continuation of application No. 15/888,675, filed on Feb. 5, 2018, now Pat. No. 9,987,400, which is a continuation of application No. 15/795,567, filed on Oct. 27, 2017, now Pat. No. 9,919,080.

(51) Int. Cl.

| | | |
|---|---|---|
| A61L 27/54 | (2006.01) | |
| A61J 1/00 | (2006.01) | |
| A61L 31/06 | (2006.01) | |
| A61N 1/37 | (2006.01) | |
| A61N 1/375 | (2006.01) | |

(56) References Cited

OTHER PUBLICATIONS

International Search Report and Written Opinion of the International Searching Authority, European Patent Office, PCT/US2018/053932, dated Jan. 17, 2019

Kabayadondo Maidei et al: "Early Complications After Pacemaker Implantations" In: "Cardiac Pacemakers—Biological Aspects, Clinical Applications and Possible Complications", Sep. 6, 2011 (Sep. 6, 2011), InTech, XP055536624, ISBN: 978-953-30-7639-3 DOI: 10.5772/20091.

Osman Beton et al: "Bleeding complications during cardiac electronic device implantation in patients receiving antithrombotic therapy: is there any value of local tranexamic acid?", BMC Cardiovascular Disorders, vol. 16, No. 1,Apr. 22, 2016 (Apr. 22, 2016), XP055538324, DOI: 10.1186/s12872-016-0251-1.

Oz, Mehmet, et al. "Controlled Clinical Trial of a Novel Hemostatic Agent in Cardiac Surgery," Ann Thorac Surg 2000; 69:1376-82; The Society of Thoracic Surgeons, 2000, published by Elsevier Science Inc.

Lodge, Andrew, et al. "A Novel Bioresorbable Film Reduces Postoperative Adhesions After Infant Cardiac Surgery," Ann Thorac Surg 2008; 86:614-21; The Society of Thoracic Surgeons, 2008, published by Elsevier Science Inc.

Barnard, James, et al. "A Review of Topical Hemostatic Agents for Use in Cardiac Surgery," Ann Thorac Surg 2009; 88:1377-83; The Society of Thoracic Surgeons, 2009, published by Elsevier Science Inc.

Bracey, Art, et al. "The Use of Topical Hemostatic Agents in Cardiothoracic Surgery," Ann Thorac Surg 2017; 104:353-60; The Society of Thoracic Surgeons, 2017, published by Elsevier Science Inc.

Gabay, Michael, et al. "An Essential Primer for Understanding the Role of Topical Hemostats, Surgical Sealants, and Adhesives for Maintaining Hemostasis." Pharmacotherapy 2013:33(9):935-955) doi: 10.1002/phar.1291; 2013 Pharmacotherapy Publications, Inc.

Hsu, Patrick W., et al. "Evaluation of porcine dermal collagen (Permacol) used in abdominal wall reconstruction," Journal of Plastic, Reconstructive & Aesthetic Surgery (2009) 62, 1484-1489; 2009 British Association of Plastic, Reconstructive and Aesthetic Surgeons. Published by Elsevier Ltd.

Cole, David, et al. "A pilot study evaluating the efficacy of a fully acetylated poly-N-acetyl glucosamine membrane formulation as a topical hemostatic agent," Surgery 1999;126:510-17. 1999 Mosby, Inc.

Spotnitz, William D. "Active and Mechanical Hemostatic Agents," Surgery 2007;142:S34-S38. 2007 Mosby, Inc.

De la Torre, Roger A., et al. "Hemostasis and hemostatic agents in minimally invasive surgery," Surgery 2007; 142: S39-S45. 2007 Mosby, Inc.

* cited by examiner

KITS FOR LOCAL DELIVERY OF WATER SOLUBLE AGENTS AND METHODS OF USE

CROSS-REFERENCE TO RELATED APPLICATIONS

This application is a continuation of U.S. patent application Ser. No. 15/963,227, filed on Apr. 26, 2018, which is a continuation of U.S. patent application Ser. No. 15/913,384, filed on Mar. 6, 2018, now U.S. Pat. No. 10,034,969, which is a continuation of U.S. patent application Ser. No. 15/888,675, filed on Feb. 5, 2018, now U.S. Pat. No. 9,987,400, which is a continuation of U.S. patent application Ser. No. 15/795,567, filed on Oct. 27, 2017, now U.S. Pat. No. 9,919,080. These applications are hereby incorporated by reference herein, in their entireties.

TECHNICAL FIELD

The present disclosure generally relates to kits and methods configured for anchoring an implantable medical device within a body, and more particularly to a kit that includes an anchorage device and at least one hemostatic agent that is separate from the anchorage device and methods of using the kit.

BACKGROUND

Some known anchorage devices may be used to secure an implantable medical device within a body of a patient. The anchorage device and implantable medical device can be inserted into a desired location within the body of the patient. The anchorage device can be used to help anchor or support the implantable medical device with surrounding tissue. Some known anchorage devices are used to provide temporary support to tissue during a healing process. For example, some known anchorage devices can secure one portion of tissue to another portion of tissue.

Pocket hematoma is a frequent complication following device implantation. For example, it is estimated that hematomas account for about 15 to 20% early intervention after pacemaker or Implantable Cardioverter Defibrillator (ICD) implantations. The development of a clinically significant pocket hematoma increases the risk of an infection by a factor or 7.7×. While increased use of anticoagulant therapy has been assigned as a possible cause, its use cannot be totally discounted due to the danger of thromboembolic events, including cerebral stroke. Hematomas may increase pain, require re-intervention for draining, and delay healing. There is an unmet clinical need to address postoperative bleeding in the pectoral pocket related to Cardiac Implantable Electronic Device (CIED) procedures in order to reduce the incidence of hematoma. Some anchorage devices include a hemostatic agent incorporated into the anchorage device to stop or reduce the flow of blood at a surgical site and/or speed up the blood clotting process while anchoring the implantable medical device to tissue. See, for example, U.S. patent application Ser. No. 15/582,935 filed on May 1, 2017, U.S. patent application Ser. No. 15/583,025, filed on May 1, 2017, U.S. patent application Ser. No. 15/583,086, filed on May 1, 2017, U.S. patent application Ser. No. 15/583,124, filed on May 1, 2017, and U.S. patent application Ser. No. 15/583,153, filed on May 1, 2017, which are each owned by Applicant and expressly incorporated by reference herein, in their entireties. However, the type of hemostatic agent and the amount of hemostatic agent that is directed to a target area can vary due to factors, such as, for example, the type of implantable medical device, the location of the target area, the size of the patient, etc. As such, a medical practitioner is required to have a large inventory of anchorage device wherein the anchorage devices include different hemostatic agents and/or different amounts of hemostatic agents to accommodate different types of implantable medical devices, different target areas, different size patients, etc. This disclosure describes an improvement over these prior art technologies.

SUMMARY

New kits and methods are provided to help anchor or support an implantable medical device to surrounding tissue. In one embodiment, a kit is provided that includes an anchorage device, such as, for example, a mesh substrate and a polymer that is fixed to the mesh substrate. The polymer comprises an active agent that is configured to elute over time. The kit further includes a hemostatic agent that is separate from the mesh substrate and the polymer. The active agent is configured to reduce or prevent infection while the hemostatic agent prevents or reduces bleeding at a target site.

The mesh substrate is configured to deliver the active agent locally to prevent infections of implanted medical devices, such as, for example, implanted electronic devices. The hemostatic agent is configured to be delivered to a target site before, during or after the mesh substrate is implanted within a patient. In some embodiments, the mesh substrate is coated with the polymer. In some embodiments, the polymer and the active agent are soluble in organic solvents, such as, for example, tetrahydrofuran. In some embodiments, the polymer and the active agent are dissolved in an organic solvent and are then sprayed onto the mesh substrate to provide a uniform coating. In some embodiments, the coating is homogenous. It is envisioned that homogenous coatings may be beneficial to provide more predictable results over coatings that are not homogenous since degradation rates and elution rates for example, of homogenous coatings may be predicted more accurately than degradation rates and elution rates of coatings that are not homogenous. In some embodiments, the hemostatic agent is insoluble in organic solvents. In some embodiments, the hemostatic agent is water soluble. In some embodiments, the polymer is a tyrosine polyarylate. In some embodiments, the active agent comprises at least one antibiotic. In some embodiments, the active agent comprises rifampin and minocycline. In some embodiments, the implanted electronic devices include pacemakers and neuromodulators.

In some embodiments, the hemostatic agent comprises one or more of tranexamic acid, collagen, oxidized cellulose and thrombin. In some embodiments, the hemostatic agent is provided in a solution. In some embodiments, the hemostatic agent is reconstituted at the time of surgery. In some embodiments, the hemostatic agent is configured to control between about 20 cc and about 50 cc of blood. In some embodiments, the hemostatic agent is configured to control less than 20 cc of blood. In some embodiments, the hemostatic agent is configured to control more than 50 cc of blood. In some embodiments, the hemostatic agent is configured to be effective to control bleeding for about 5 days to about 7 days. In some embodiments, the hemostatic agent is configured to be effective to control bleeding less than 5 days. In some embodiments, the hemostatic agent is configured to be effective to control bleeding for more than 7 days.

In some embodiments, the mesh substrate defines an envelope, pouch, or pocket in which, one side of the envelope, pouch, or pocket includes an opening to allow a device, such as, for example, the implantable medical device to be inserted through the opening and into a cavity of the envelope, pouch, or pocket. In some embodiments, the polymer covers all or a portion of the mesh substrate. In some embodiments, the polymer also includes an active agent such that the active pharmaceutical agent elutes over time in the area surrounding or adjacent to the mesh substrate. In some embodiments, the polymer including the active agent is applied to the mesh substrate such that the active agent elutes over time in the area surrounding or adjacent to the mesh substrate.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
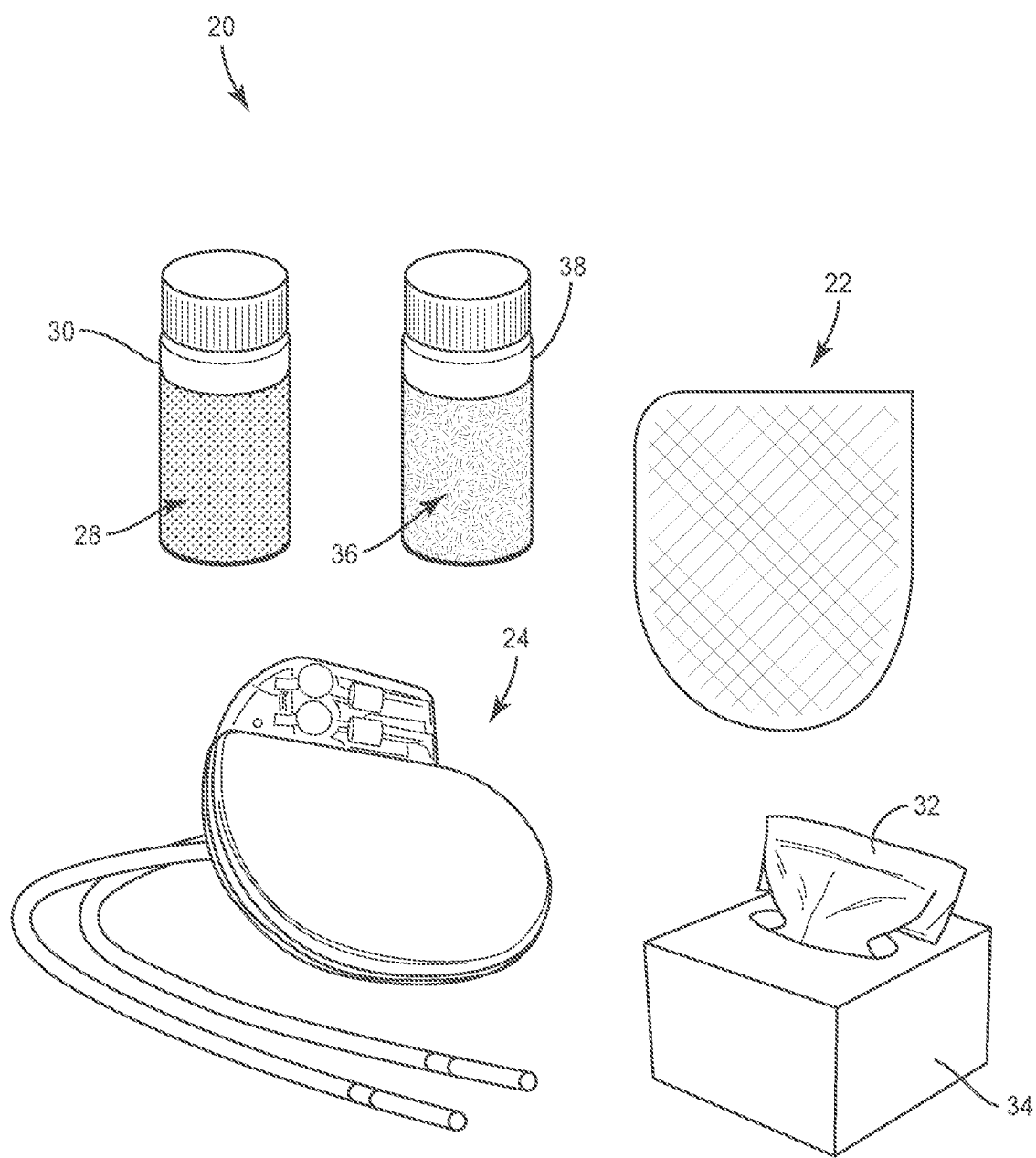
FIG. 1 is a perspective view of components of a kit in accordance with the principles of the present disclosure.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

This disclosure is directed to a kit 20 that include at least one anchorage device. In some embodiments, the components of kit 20 can be fabricated from biologically acceptable materials suitable for medical applications, including metals, synthetic polymers, allografts, xenografts, isografts, ceramics and bone material and/or their composites, depending on the particular application and/or preference of a medical practitioner. For example, the components of kit 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, tyrosine polyarylate, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polylactide, polyglycolide, polytyrosine carbonate, polycaroplactone and their combinations.

Various components of kit 20 may have material composites, including the above materials, to achieve various desired characteristics such as strength, rigidity, elasticity, compliance, biomechanical performance, durability and radiolucency or imaging preference. The components of kit 20, individually or collectively, may also be fabricated from a heterogeneous material such as a combination of two or more of the above-described materials. The components of kit 20 may be monolithically formed, integrally connected or include fastening elements and/or instruments, as described herein.

Figure 2:
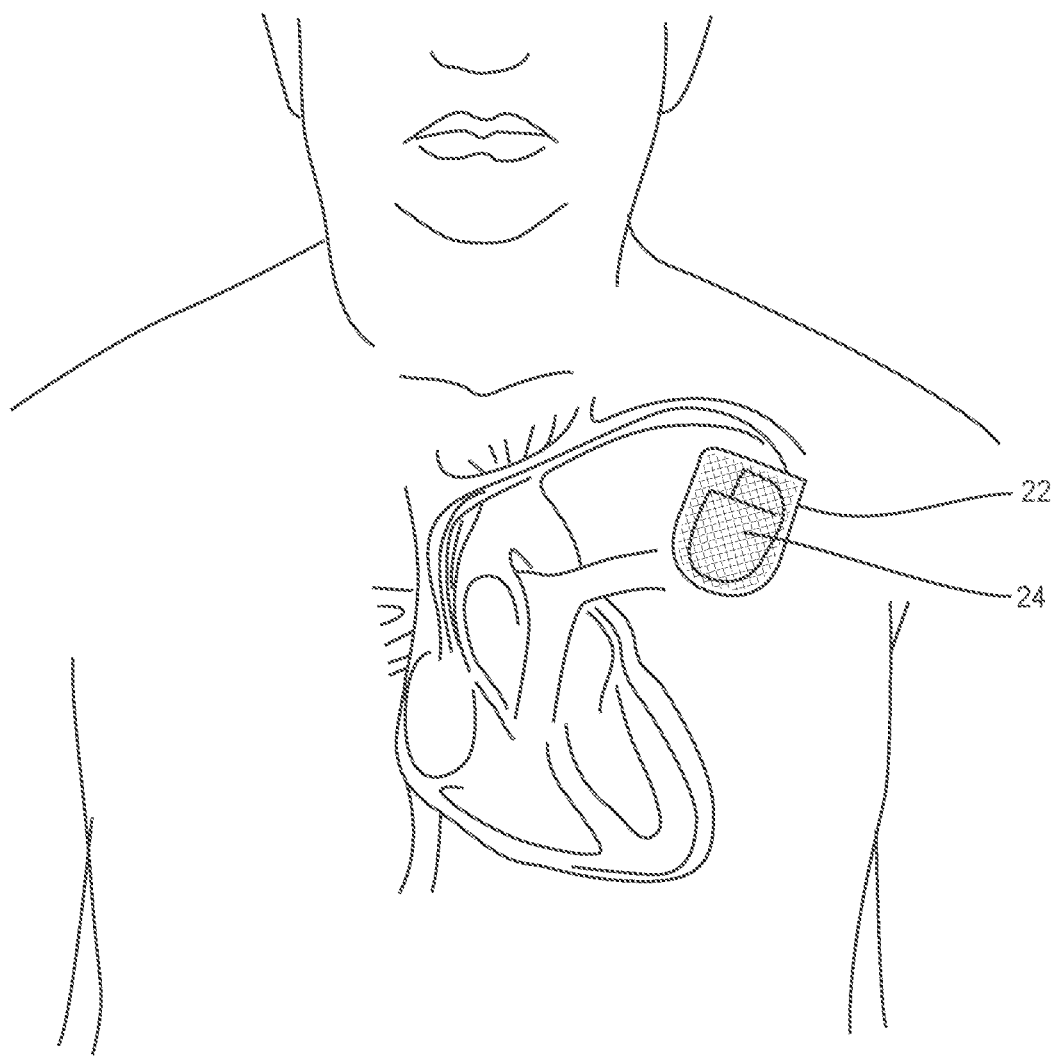
FIG. 2 is a front view of components of the kit shown in FIG. 1 implanted in a patient.

Kit 20 includes a substrate, such as, for example, mesh substrate 22, as shown in FIG. 1. Substrate 22 is configured to be coupled to and/or applied to a device, such as, for example, an implantable medical device 24, as shown in FIG. 2. In some embodiments, substrate 22 is configured to surround and/or enclose at least a portion of implantable medical device 24, as discussed herein. Substrate 22 is configured to be secured to tissue to support implantable medical device 24 at a treatment site.

Substrate 22 can have a variety of different configurations, shapes and sizes. For example, substrate 22 can be provided with a size and shape or other configuration that can provide the functionality of supporting and immobilizing implantable medical device 24 at a target site, such as, for example, a treatment site within a patient's body, while also improving the removability of substrate 22 after the treatment has been completed. In some embodiments, implantable medical device 24 can be disposed within a pocket defined by substrate 22 and substrate 22 can be implanted and secured to tissue at a desired treatment site within a body of a patient. As discussed herein, during implantation, scar tissue can form at the treatment site and/or tissue can become ingrown within substrate 22. After the treatment is completed, implantable medical device 24 can remain in the patient, or can be removed from the patient leaving substrate implanted, as discussed herein. To remove substrate 22, tissue that is ingrown within substrate 22 can be cut or otherwise detached from substrate 22. In some embodiments, a portion of substrate 22 may not be removable from the tissue and will remain implanted within the patient.

Substrate 22 may be formed with one or more biocompatible materials, which may be synthetic or naturally occurring. In some embodiments, the one or more biocompatible materials include, for example, polypropylene, polyester, polytetrafluoroethylene, polyamides, silicones, polysulfones, metals, alloys, titanium, stainless steel, shape memory metals (e.g. Nitinol), and/or combinations thereof.

In some embodiments, substrate 22 is configured to be implanted temporarily within a body of a patient and/or is configured to be removed (e.g., explanted) from the patients body after a period of time. In such embodiments, substrate 22 may include a non-biodegradable material and/or a non-bioresorbable material. For example, substrate 22 may be made entirely from a non-biodegradable material and/or a non-bioresorbable material such that substrate 22 is made only from the non-biodegradable material and/or non-bioresorbable material. In some embodiments, substrate 22 may include one or more non-biodegradable and/or a non-bioresorbable material and one or more biodegradable and/or resorbable material. In some embodiments, one side of substrate 22 may include one or more non-biodegradable and/or a non-bioresorbable material and another side of substrate 22 can include one or more biodegradable and/or resorbable material.

As used herein, the term "biodegradable" refers to, for example, a material that can be at least partially broken down or degraded by a bodily fluid and discarded as waste from the body and/or a material that can be broken down or degraded by a living organism. Thus, "non-biodegradable" can refer to a material that cannot be broken down or degraded by a bodily fluid and/or cannot be broken down or degraded by a living organism. As used herein the term "resorbable" refers to, for example, a material that can be at least partially broken down or degraded by a bodily fluid and assimilated within the body. Thus, a "non-resorbable" material as used herein can refer to, for example, a material that cannot be broken down or degraded by bodily fluid and assimilated within the body.

In some embodiments, the biocompatible biodegradable and/or bioresorbable material or materials may include polymeric and/or non-polymeric materials, such as, for example, one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), polyorthoesters (POE), polyaspirins, polyphosphazenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, tyrosine polyarylates, polyetheretherketone, polymethylmethacrylate, silicone, hyaluronic acid, chitosan, or combinations thereof. In one embodiment, substrate 22 comprises Glycoprene, which is sold by Poly-Med, Inc. As used herein, the term "glycoprene" or "Glycoprene" refers to Glycoprene® or Glycoprene II. Glycoprene® can refer to different variations of the material sold under the trade name Glycoprene®, such as, for example, Glycoprene 6829, Glycoprene 8609 and Glycoprene®7027.

In some embodiments, the biocompatible non-biodegradable and/or non-bioresorbable material or materials may include polymeric and/or non-polymeric materials, such as, for example, polyurethane, polyester, polytetrafluoroethylene (PTFE), polyethylacrylate/polymethylmethacrylate, polylactide, polylactide-co-glycolide, polyamides, polydioxanone, polyvinyl chloride, polymeric or silicone rubber, collagen, thermoplastics, or combinations thereof.

In some embodiments, substrate 22 is configured to be permanently implanted within a body of a patient. In such embodiments, substrate 22 may include a biodegradable material and/or a bioresorbable material. For example, substrate 22 may be made entirely from a biodegradable material and/or a bioresorbable material such that substrate 22 is made only from the biodegradable material and/or bioresorbable material.

Figure 3:
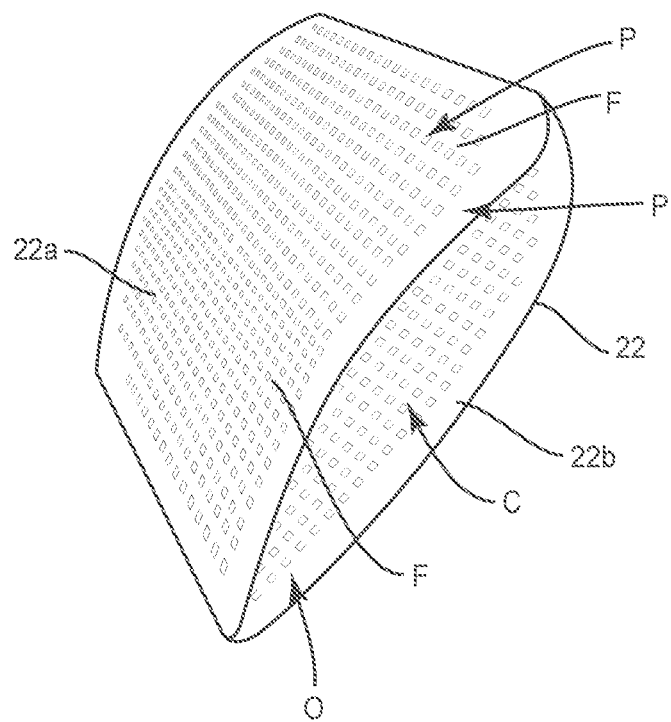
FIG. 3 is a perspective view of a component of the kit shown in FIG. 1.

In some embodiments, substrate 22 is web or fabric with a construction of knitted, braided, woven or non-woven filaments or fibers F that are interlocked in such a way to create a fabric or a fabric-like material that includes a matrix of filaments that define multiple pores P, as shown in FIG. 3. That is, the space between adjacent filaments or fibers F define pores P of the mesh. Pores P may be beneficial to allow tissue in-growth, for example. In some embodiments, apertures may be formed in the mesh by cutting the filaments or fibers F to decrease the areal density (e.g., surface density) or mass of the mesh and/or further facilitate tissue in-growth. In some embodiments, the apertures that extend through the filaments or fibers F are larger than pores P defined by the filaments or fibers F.

In some embodiments, substrate 22 is provided in the form of a thin walled structure, such as, for example, a wafer, sheet or tissue. In some embodiments, the thin walled structure does not include any pores or apertures, in contrast to the mesh discussed herein. In some embodiments, the thin walled structure includes pores or apertures that are smaller than the pores or apertures of the mesh discussed herein. In some embodiments, the thin walled structure has a thickness that is less than a thickness of the mesh discussed herein. In some embodiments, the thickness of the thin walled structure is between about 0.001 inches and about 0.1 inches.

In some embodiments, substrate 22 is a planar sheet, as shown in FIG. 1. In some embodiments, the planar sheet is in the form of a mesh. In some embodiments, the planar sheet is in the form of a thin walled structure. The planar sheet has a first side and an opposite second side, similar to a sheet of paper. The planar sheet can be manipulated about all or only a portion of an implantable medical device, such as, for example, one of the implantable medical devices discussed herein. In some embodiments, the planar sheet is moldable or bendable about the implantable medical device. That is, the planar sheet can be bent without breaking the planar sheet. In some embodiments, the planar sheet can be manipulated to form a tube, for example. In some embodiments, the planar sheet has a rigid configuration. That is, the planar sheet cannot be bent without breaking the planar sheet. In some embodiments, the planar sheet can be secured to tissue to support the implantable medical device at the treatment site. The planar sheet can be variously shaped, such as, for example, circular, oval, oblong, triangular, rectangular, square, polygonal, irregular, uniform, non-uniform, variable and/or tapered.

In some embodiments, substrate 22 is a scaffold, a sponge, woven, non-woven, knitted or non-knitted. In some embodiments, substrate 22 can be formed by extrusion.

In some embodiments, substrate 22 is a pocket or envelope in which implantable medical device 24 can be at least partially disposed. That is, substrate 22 is a pouch, bag, covering, shell, or receptacle. For example, substrate 22 can include a first piece 22a and a second piece 22b that is joined with first piece 22a, as shown in FIG. 3. First and second pieces 22a, 22b are joined to form the pocket or envelope. In some embodiments, first and second pieces 22a, 22b are joined along three sides of the pocket or envelope to form a cavity C. First and second pieces 22a, 22b are not joined at a fourth side of the pocket or envelope to define an opening O such that implantable medical device 24 can be inserted through opening O and into cavity C to enclose, encase or surround all or a portion of implantable medical device 24 within cavity C. In some embodiments, first and second pieces 22a, 22b are joined with one another along three sides of the pocket or envelope by heat, ultrasonically, bonding, knitting, or adhesive. In some embodiment, the pocket or envelope is monolithically formed by molding the pocket or envelope or producing the pocket or envelope by 3D printing, for example.

Figure 4:
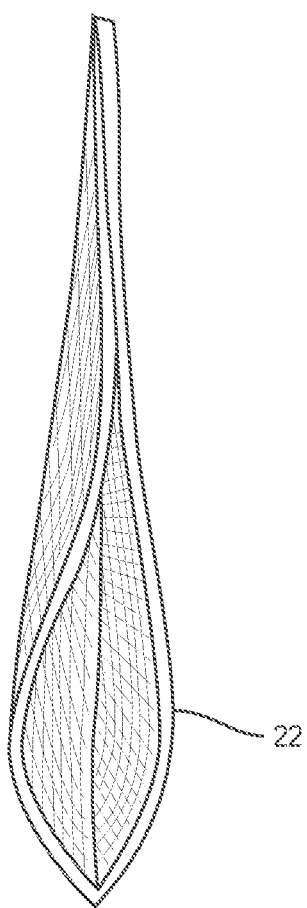
FIG. 4 is a perspective view of a component of the kit shown in FIG. 1.

In some embodiments, first and second pieces 22a, 22b are portions of a single sheet that is bent to produce a fold at one end of the pocket or envelope, as shown in FIG. 4. First and second pieces 22a, 22b are joined along sides of the pocket or envelope that extend transverse to the fold such that the fold and the sides of the pocket or envelope do not have any openings. First and second pieces 22a, 22b are not joined at an end of the pocket or envelope opposite the fold to define an opening at the end such that a medical device can be inserted through the opening and into a cavity defined by inner surfaces of first and second pieces 22a, 22b.

In some embodiments, first and second pieces 22a, 22b each include a mesh discussed herein. In some embodiments, first piece 22a includes a mesh including pores having a first size and second piece 22b includes a mesh including pores having a second size, wherein the first size is different than the first size. In some embodiments, the first size is greater than the second size. In some embodiments, the first size is less than the second size. In some embodiments, first and second pieces 22a, 22b each include a thin walled structure discussed herein. In some embodiments one of first and second pieces 22a, 22b includes a mesh discussed herein and the other one of first and second pieces 22a, 22b includes a thin walled structure discussed herein that does not have any pores or apertures.

In some embodiments, first and second pieces 22a, 22b are formed from the same material. In some embodiments one of first and second pieces 22a, 22b is formed from a first material, such as, for example, one of the materials discussed herein, and the other one of first and second pieces 22a, 22b is made from a second material, such as, for example, one of the materials discussed herein, wherein the second material is different than the first material. For example, first piece 22a may be formed from a biodegradable and/or bioresorbable material and second piece 22b may be formed from a non-biodegradable and/or non-bioresorbable material, or vice versa. In some embodiments, first and second pieces 22a, 22b are each formed from a biodegradable and/or bioresorbable material, wherein the biodegradable and/or bioresorbable materials degrade and/or resorb at the same rate. In some embodiments, first and second pieces 22a, 22b are formed from different biodegradable and/or bioresorbable materials, wherein one of the biodegradable and/or bioresorbable materials degrades and/or resorbs more quickly than the other biodegradable and/or bioresorbable material.

In some embodiments, first and second pieces 22a, 22b each include a single layer of material, such as, for example, one of the materials discussed herein. In some embodiments, at least one of first and second pieces 22a, 22b includes multiple layers. In some embodiments, the multiple layers include more than one layer of the mesh discussed herein. In some embodiments, the multiple layers include more than one layer of the thin walled structure discussed herein. In some embodiments, the multiple layers include one or more layer of the mesh discussed herein and one or more layer of the thin walled structure discussed herein. In some embodiments, the multiple layers include one or more layer of the mesh discussed herein and one or more layer of the thin walled structure discussed herein, wherein one of the layers of mesh is positioned between two layers of the thin walled structure. In some embodiments, the multiple layers include one or more layer of the mesh discussed herein and one or more layer of the thin walled structure discussed herein, wherein one of the layers of thin walled structure is positioned between two layers of the mesh.

In some embodiments, substrate 22 may include a polymer that is applied to and/or coats at least a portion of substrate 22, wherein the polymer includes an active agent, such as, for example an active pharmaceutical agent That is, the active pharmaceutical agent is applied to substrate 22 via the polymer. In some embodiments, the polymer is soluble in organic solvents, such as, for example, tetrahydrofuran. In some embodiments, the active pharmaceutical agent is also soluble in organic solvents, such as, for example, tetrahydrofuran. In some embodiments, the polymer and the active pharmaceutical agent are dissolved in an organic solvent and the organic solvent with the dissolved polymer and active pharmaceutical agent is sprayed onto substrate 22 to provide a uniform coating. In some embodiments, the polymer includes a combination, blend or mixture of polymers. In some embodiments, the polymer is configured to degrade within a patient and releases the active pharmaceutical agent as the polymer degrades. In some embodiments, the degradation rate of the polymer is known or can be predicted to allow a medical practitioner to select a polymer or a quantity of polymer that is applied to substrate 22 to produce substrate 22 that is customized to elute a selected quantity of the active pharmaceutical agent at a selected rate over a selected period of time. For example, the polymer may be selected to elute a selected quantity of the active pharmaceutical agent per hour or day for a selected number of days or hours.

In some embodiments, the polymer is selected from the group consisting of polylactic acid, polyglycolic acid, poly (L-lactide), poly(D,L-lactide)polyglycolic acid[polyglycolde], poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), polydepsipeptides, maleic anhydride copolymers, polyiminocarbonates, poly [(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose. In some embodiments, the polymer may include combinations, blends or mixtures of the polymers discussed herein.

In some embodiments, the polymer is a polyarylate. In some embodiments, the polymer is a tyrosine-derived polyarylate. In some embodiments, the tyrosine-derived polyarylate is p(DTE co X % DT succinate), where X is about 10% to about 30%. In some embodiments, the tyrosine-derived polyarylate is p(DTE co X % DT succinate), where X ranges from about 26.5% to about 28.5%. In some embodiments, the tyrosine-derived polyarylate is p(DTE co X % DT succinate), where X is about 27.5%. In some embodiments, the polymer is P22-27.5 DT.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22-XX is a polyarylate copolymer produced by condensation of DTE and DTBn with succinic acid followed by removal of benzyl group. P22-10, P22-15, P22-20, P22-XX, etc., represents copolymers different percentage of DT (i.e., 10, 15, 20 and % DT, etc.). In some embodiments, the polymer is produced by condensation of DTBn with succinic acid followed by removal of benzyl group.

In some embodiments, the polymer includes one or more polyarylates that are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. In some embodiments, the DT or BT contents include those copolymers with from about 1% to about 30%, from about 5% to about 30% from about 10 to about 30% DT or BT. In some embodiments, the diacids (used informing the polyarylates) include succinate, glutarate and glycolic acid.

In some embodiments, the polymer includes one or more biodegradable, resorbable polyarylates and polycarbonates. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P (Desaminotyrsoyl tyrosine methylparaben ester-glutarate), and DTPP P (Desaminotyrsoyl tyrosine propylparaben ester-glutarate).

In some embodiments, the polymer is one more polymers from the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT. In some embodiments, the polymer is P22-27.5 DT.

In some embodiments, the polymer has diphenol monomer units that are copolymerized with an appropriate chemical moiety to form a polyarylate, a polycarbonate, a polyiminocarbonate, a polyphosphonate or any other polymer.

In some embodiments, the polymer is tyrosine-based polyarylate. In some embodiments, the polymer includes blends and copolymers with polyalkylene oxides, including polyethylene glycol (PEG).

In some embodiments, the polymer can have from 0.1-99.9% PEG diacid to promote the degradation process. In some embodiments, the polymer includes blends of polyarylates or other biodegradable polymers with polyarylates.

The polymer is configured to release the active pharmaceutical agent over time, as discussed herein. In some embodiments, the polymer is configured to release the active pharmaceutical agent over a time period ranging from about 1 hour to about 168 hours. In some embodiments, the polymer is configured to release the active pharmaceutical agent over a time period ranging from 1 hour to 72 hours. In some embodiments, the polymer is configured to release the active pharmaceutical agent over a time period ranging from 1 hour to 24 hours.

In some embodiments, the polymer is configured to release the active pharmaceutical agent over time in an area surrounding or adjacent to substrate 22 (such as, for example, within the "pocket" or within 3 inches in all dimensions). In some embodiments, the polymer is configured to release the active pharmaceutical agent for up to 30 hours. In some embodiments, the polymer is configured to release between about 40% and about 100% of the active pharmaceutical agent over a period of at least about 30 hours. In some embodiments, the polymer is configured to release between about 60% and about 100% of the active pharmaceutical agent over a period of at least about 30 hours. In some embodiments, the polymer is configured to release between about 65% and about 100% of the active pharmaceutical agent over a period of at least about 36 hours. In some embodiments, the polymer is configured to release between about 80% and about 100% of the active pharmaceutical agent over a period of at least about 36 hours. In some embodiments, the polymer is configured to release between about 60% and about 100% of the active pharmaceutical agent over a period of at least about 48 hours. In some embodiments, the polymer is configured to release between about 80% and about 100% of the active pharmaceutical agent over a period of at least about 48 hours. In some embodiments, the polymer is configured to release between about 60% and about 100% of the active pharmaceutical agent over a period of at least about 60 hours. In some embodiments, the polymer is configured to release between about 80% and about 100% of the active pharmaceutical agent over a period of at least about 60 hours. In some embodiments, the polymer is configured to release between about 80% and about 100% of the active pharmaceutical agent within 48 hours. In some embodiments, the polymer is configured to release between about 80% and about 100% of the active pharmaceutical agent within 24 hours.

In some embodiments, the polymer is configured to release no more than 60% of the active pharmaceutical agent within 24 hours. In some embodiments, the polymer is configured to release no more than 90% of the active pharmaceutical agent after 60 hours. In some embodiments, the polymer is configured to release no more than 50% of the active pharmaceutical agent within 12 hours. In some embodiments, the polymer is configured to release between about 40% and about 90% of the active pharmaceutical agent between 12 and 24 hours. In some embodiments, the polymer is configured to release between about 60% and about 100% of the active pharmaceutical agent between 24 and 36 hours. In some embodiments, the polymer is configured to release between about 65% and about 100% of the active pharmaceutical agent between 36 and 48 hours. In some embodiments, the polymer is configured to release between about 70% and about 100% of the active pharmaceutical agent between 48 and 60 hours.

Substrate 22 may be coated with single or multiple coating layers of the polymer, depending on, for example, the amount of the active pharmaceutical agent to be delivered and desired release rate. Each layer of the polymer may contain the same or different amounts of the active pharmaceutical agent. For example, a first layer of the polymer may contain the active pharmaceutical agent, while the second layer of the polymer contains either no active pharmaceutical agent or a lower concentration of the active pharmaceutical agent. As another example, a first layer of the polymer may comprise the active pharmaceutical agent in a first polymer, while the second layer of the polymer comprises the active pharmaceutical agent in a second polymer that is different than the first polymer.

In embodiments discussed herein wherein substrate 22 is a planar sheet, a first polymer can be applied to the top surface of the sheet and a second polymer can be applied to the bottom surface of the sheet. In some embodiments, the first and second polymers are different polymers. In some embodiments, the first and second polymers release the active pharmaceutical agent at different rates and/or over different lengths of time. In some embodiments, the first and second polymers are different polymers, and the first polymer includes a first amount of the active pharmaceutical agent and the second polymer includes a second amount of the active pharmaceutical agent, the first amount being different than the second amount. In some embodiments, the first and second polymers are the same polymer, wherein the first polymer includes a first amount of the active pharmaceutical agent and the second polymer includes a second amount of the active pharmaceutical agent, the first amount being different than the second amount.

In embodiments discussed herein wherein substrate 22 is a pocket or envelope, a first polymer can be applied to first piece 22a and a second polymer can be applied to second piece 22b. In some embodiments, the first and second polymers are different polymers. In some embodiments, the first and second polymers release the active pharmaceutical agent at different rates and/or over different lengths of time. In some embodiments, the first and second polymers are different polymers, and the first polymer includes a first amount of the active pharmaceutical agent and the second polymer includes a second amount of the active pharmaceutical agent, the first amount being different than the second amount. In some embodiments, the first and second polymers are the same polymer, wherein the first polymer includes a first amount of the active pharmaceutical agent and the second polymer includes a second amount of the active pharmaceutical agent, the first amount being different than the second amount. In some embodiments, a first polymer is applied to the outer surfaces of first and second pieces 22a, 22b and a second polymer is applied to the inner surfaces of first and second pieces 22a, 22b, wherein the first polymer includes a first amount of the active pharmaceutical agent and the second polymer includes a second amount of the active pharmaceutical agent, the first amount being different than the second amount. In some embodiments, the first amount is more than the second amount. In some embodiments, the first amount is less than the second amount.

In some embodiments, the polymer and/or the active pharmaceutical agent is/are free of hemostatic agents, such as, for example, the hemostatic agents discussed herein, such that substrate 22 does not include any hemostatic agents. In some embodiments, the active pharmaceutical agent can include one or a combination of active pharmaceutical ingredients, such as, for example, anesthetics, antibiotics, anti-inflammatory agents, procoagulant agents, fibrosis-inhibiting agents, antiseptics, anti-scarring agents, leukotriene inhibitors/antagonists, cell growth inhibitors and mixtures thereof. In some embodiments, the active pharmaceutical ingredient is an antibiotic. In some embodiments, the antibiotic is selected from the group consisting of rifampin and minocycline and mixtures thereof.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antibacterial agents or antimicrobials include, but are not limited to, triciosan, chlorhexidine and other cationic biguanides, rifampin, minocycline (or other tetracycline derivatives), vancomycin, gentamycin; gendine; genlenol; genfoctol; clofoctol; cephalosporins and the like. Further antibacterial agents or antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; hexachlorophene; cefamandole nafate; cefepime and its hydrochloride, sulfate, and phosphate salt; cefdinir and its sodium salt; ceftriaxone and its sodium salt; cefixime and its sodium salt; cetylpyridinium chloride; ofoxacin; linexolid; temafloxacin; fleroxacin; enoxacin; gemifloxacin; lomefloxacin; astreonam; tosufloxacin; clinafloxacin; cefpodoxime proxetil; chloroxylenol; methylene chloride, iodine and iodophores (povidone-iodine); nitrofurazone; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, dindamycin; dindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; α-terpineol; thymol; taurinamides; nitrofurantoin; silver-sulfadiazine; hexetidine; methenamine; aldehydes; azylic acid; silver; benzyl peroxide; alcohols; carboxylic acids; salts; nafcillin; ticarcillin and its disodium salt; sulbactam and its sodium salt; methylisothiazolone, moxifloxacin; amifloxacin; pefloxacin; nystatin; carbepenems; lipoic acids and its derivatives; beta-lactams antibiotics; monobactams; aminoglycosides; microlides; incosamides; glycopeptides; tetracyclines; chloramphenicol; quinolones; fucidines; sulfonamides; macrolides; ciprofloxacin; ofloxacin; levofloxacins; teicoplanin; mupirocin; norfloxacin; sparfloxacin; ketolides; polyenes; azoles; penicifins; echinocandines; nalidixic acid; rifamycins; oxalines; streptogramins; lipopeptides; gatifloxacin; trovafloxacin mesylate; alatrofloxacin mesylate; trimethoprims; sulfamethoxazole; demeclocydine and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin (and combinations thereof). In some embodiments, the polymer may contain rifampin and another antimicrobial agent, such as, for example, an antimicrobial agent that is a tetracycline derivative. In some embodiments, the polymer contains a cephalosporin and another antimicrobial agent. In some embodiments, the polymer contains combinations including rifampin and minocycline, rifampin and gentamycin, and rifampin and minocydine.

When a mixture of two antibiotics is used, they generally present in a ratio ranging from about 10:1 to about 1:10. In some embodiments, a mixture of rifampin and minocycline are used. In those embodiments, a ratio of rifampin to minocycline ranges from about 52 to about 2:5. In other embodiments, the ratio of rifampin to minocycline is about 1:1.

Examples of antifungals include amphotericin B; pyrimethamine; flucytosine; caspofungin acetate; fluconazole; griseofulvin; terbinafine and its hydrochloride, sulfate, or phosphate salt; amorolfine; triazoles (Voriconazole); flutrimazole; cilofungin; LY303366 (echinocandines); pneumocandin; imidazoles; omoconazole; terconazole; fluconazole; amphotericin B, nystatin, natamycin, liposomal amptericin B, liposomal nystatins; griseofulvin; BF-796; MTCH 24; BTG-137586; RMP-7/Amphotericin B; pradimicins; benanomicin; ambisome; ABLC; ABCD; Nikkomycin Z; flucytosine; SCH 56592; ER30346; UK 9746; UK 9751; T 8581; LY121019; ketoconazole; micronazole; clotrimazole; econazole; ciclopirox; naftifine; and itraconazole.

In some embodiments, the active pharmaceutical ingredient includes keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proHne, melphalan, penicillin V, aspirin, nicotinic acid, chemodeoxycholic acid, chlorambucil, paclitaxel, sirolimus, cydosporins, 5-fluorouracil and the like.

In some embodiments, the active pharmaceutical ingredient includes one or more ingredients that act as angiogenesis inhibitors or inhibit cell growth such as epidermal growth factor, PDGF, VEGF, FGF (fibroblast growth factor) and the like. These ingredients include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compounds include, but are not limited to, anecortive acetate; tetrahydrocortisol, 4,9(11)-pregnadien-17α, 21-diol-3,20-dione and its −21-acetate salt; 111-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its −21-acetate, −21-disodium phosphate, and −21-hemisuccinate forms; triamcinolone benetonide; triamcinolone hexacetonide; fluocinolone and fluocinolone acetate; dexamethasone and its −21-acetate, −21-(3,3-dimethylbutyrate), −21-phosphate disodium salt, −21-diethylaminoacetate, −21-isonicotinate, −21-dipropionate, and −21-palmitate forms; betamethasone and its −21-acetate, −21-adamantoate, −17-benzoate, −17,21-dipropionate, −17-valerate, and −21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verdukast, zafirukast, and zileuton.

In some embodiments, the active pharmaceutical ingredient includes sodium 2-mercaptoethane sulfonate ("MESNA"). MESNA has been shown to diminish myofibroblast formation in animal studies of capsular contracture with breast implants [Ajmal et al. (2003) Plast Reconstr. Surg. 112:1455-1461] and may thus act as an anti-fibrosis agent.

Procoagulants include, but are not limited to, zeolites, thrombin, and coagulation factor concentrates.

In some embodiments, the amount of the active pharmaceutical ingredient that is applied to substrate 22 via the polymer ranges between about 0.3 to about 150 micrograms/cm$^2$. In other embodiments, the amount of the active pharmaceutical ingredient that is applied to substrate 22 via the polymer ranges between about 0.6 to about 1.4 micrograms/cm$^2$. In yet other embodiments, the amount of the active pharmaceutical ingredient that is applied to substrate 22 via the polymer ranges between about 0.85 to about 1.20 micrograms/cm$^2$. In yet further embodiments, the amount of the active pharmaceutical ingredient that is applied to substrate 22 via the polymer ranges between about 0.90 to about 1.10 micrograms/cm$^2$. In yet further embodiments, the amount of the active pharmaceutical ingredient that is applied to substrate 22 via the polymer ranges between about 50 to about 150 micrograms/cm$^2$. In yet further embodiments, 62 micrograms/cm$^2$ of the active pharmaceutical ingredient is applied to substrate 22 via the polymer. In yet further embodiments, 140 micrograms/cm$^2$ of the active pharmaceutical ingredient is applied to substrate 22 via the polymer.

In other embodiments, the active pharmaceutical ingredient includes rifampin and minocydine and the amount of each of rifampin and minocycline that is applied to substrate 22 via the polymer ranges between about 0.6 to about 1.4 micrograms/cm$^2$. In yet other embodiments, the amount of each of rifampin and minocycline that is applied to substrate 22 via the polymer ranges between about 0.85 to about 1.20 micrograms/cm$^2$. In yet further embodiments, the amount of each of rifampin and minocycline that is applied to substrate 22 via the polymer ranges between about 0.90 to about 1.10 micrograms/cm$^2$.

The active pharmaceutical agent may include any of the active pharmaceutical ingredients discussed herein. Doses of the active pharmaceutical ingredients discussed herein are known and the amounts of any single active pharmaceutical ingredient to include in the polymer can readily be surmised. Any pharmaceutically acceptable form of the active pharmaceutical ingredients discussed herein can be employed in substrate 22 and/or the polymer, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

In embodiments discussed herein wherein anchorage device 20 is a planar sheet, the polymer including the active pharmaceutical agent can be applied to at least one of the top and bottom surfaces of the sheet via the polymer. That is, the polymer may be applied to both the top and bottom surfaces, or only one of the top and bottom surfaces. In some embodiments, a first polymer including an active pharmaceutical agent is applied to the top surface and a second polymer including an active pharmaceutical ingredient is applied to the bottom surface, wherein the first polymer includes an active pharmaceutical ingredient that is different than the active pharmaceutical ingredient in the second polymer. In some embodiments, a first polymer including an active pharmaceutical ingredient is applied to the top surface and a second polymer including an active pharmaceutical ingredient is applied to the bottom surface, wherein the active pharmaceutical ingredient in the first polymer includes a different amount of active pharmaceutical ingredient than the second polymer.

In embodiments discussed herein wherein substrate 22 is a planar sheet, the polymer including the active pharmaceutical ingredient can be applied to the top surface and the bottom surface is free of the polymer. In some embodiments, one of the top and bottom surfaces includes the polymer including the active pharmaceutical ingredient and the other of the top and bottom surfaces is free of the polymer. In some embodiments, one of the top and bottom surfaces includes the polymer including the active pharmaceutical ingredient and the other of the top and bottom surfaces includes a polymer that is free of any active pharmaceutical ingredients.

In embodiments discussed herein wherein substrate 22 is a planar sheet, a first polymer can be applied to one of the top and bottom surfaces and a second polymer can be applied to the other one of the top and bottom surfaces. In some embodiments, at least one of the first and second polymers includes a plurality of discrete layers, such as, for example, a first layer, a second layer, a third layer, a fourth layer, a fifth layer, etc. In some embodiments, at least one of the layers includes a polymer that is different than a polymer that forms at least one of the other layers.

In some embodiments, the layers each include the same polymer. In some embodiments, the contents of the layers alternate. For example, in some embodiments, the first layer includes the active pharmaceutical agent, the second layer is free of the active pharmaceutical agent, the third layer includes the active pharmaceutical agent, the fourth layer is free of the active pharmaceutical agent and the fifth layer includes the active pharmaceutical agent. In some embodiments, the layers each include the active pharmaceutical agent, wherein the amount of the active pharmaceutical agent in each layer is the same or different.

In embodiments discussed herein wherein substrate 22 is a pocket or envelope, the polymer including the active pharmaceutical agent can be applied to at least one of first piece 22a and second piece 22b. In some embodiments, only one of first and second pieces 22a, 22b includes the polymer having the active pharmaceutical ingredient. In some embodiments, the polymer including the active pharmaceutical ingredient is applied only to the outer surfaces of first and second pieces 22a, 22b. That is, the inner surfaces of first and second pieces 22a, 22b that define cavity C do not have the polymer applied thereto. In some embodiments, the polymer including the active pharmaceutical ingredient is applied only to the inner surfaces of first and second pieces 22a, 22b. That is, the outer surfaces of first and second pieces 22a, 22b do not have the polymer applied thereto. In some embodiments, the polymer including the active pharmaceutical ingredient is applied only to the inner surface of one of first and second pieces 22a, 22b and to the outer surface of the other one of first and second pieces 22a, 22b.

In embodiments discussed herein wherein substrate 22 is a pocket or envelope, a polymer having a first active pharmaceutical ingredient can be applied to first piece 22a and a polymer having a second active pharmaceutical ingredient can be applied to second piece 22b, wherein the active pharmaceutical ingredient in the second polymer is different than the active pharmaceutical ingredient in the first polymer. In some embodiments, a first polymer including an active pharmaceutical ingredient is applied to the outer surfaces of first and second pieces 22a, 22b and a second polymer including an active pharmaceutical ingredient is applied to the inner surfaces of first and second pieces 22a, 22b, wherein the active pharmaceutical ingredient in the second polymer is different than the active pharmaceutical ingredient in the second polymer.

In embodiments discussed herein wherein substrate 22 is a pocket or envelope, a first polymer can be applied to one of first and second pieces 22a, 22b and a second polymer can be applied to the other one of first and second pieces 22a, 22b. In some embodiments, the first and second polymers are the same polymer. In some embodiments, the first and second polymers are different polymers. In some embodiments, the first and second polymers each include the active pharmaceutical ingredient, wherein one of the first and second polymers includes more of the active pharmaceutical ingredient than the other of the first and second polymers.

In embodiments discussed herein wherein anchorage device 20 is a pocket or envelope, a first polymer can be applied to first piece 22a and a second polymer can be applied to second piece 22b. In some embodiments, the first and second polymers are different polymers. In some embodiments, the first and second polymers release the active pharmaceutical ingredient at different rates and/or over different lengths of time. In some embodiments, the first and second polymers are different polymers, and the first polymer includes a first amount of the active pharmaceutical ingredient and the second polymer includes a second amount of the active pharmaceutical ingredient, the first amount being different than the second amount. In some embodiments, the first and second polymers are the same polymer, wherein the first polymer includes a first amount of the active pharmaceutical ingredient and the second polymer includes a second amount of the active pharmaceutical ingredient, the first amount being different than the second amount. In some embodiments, a first polymer is applied to the outer surfaces of first and second pieces 22a, 22b and a second polymer is applied to the inner surfaces of first and second pieces 22a, 22b, wherein the first polymer includes a first amount of the active pharmaceutical ingredient and the second polymer includes a second amount of the active pharmaceutical ingredient, the first amount being different than the second amount. In some embodiments, the first amount is more than the second amount. In some embodiments, the first amount is less than the second amount.

In some embodiments, the active pharmaceutical ingredient is configured to elute/release from the polymer into an area surrounding or adjacent to substrate 22 to reduce the amount of associated post-surgical complications that can occur with such implantable medical devices, such as, for example, post-implant infection, pain, excessive scar tissue formation and shrinkage of the prosthesis or mesh, excessive scar tissue formation, limited patient mobility, and/or chronic pain. In some embodiments, the active pharmaceutical ingredient is configured to elute/release from the polymer into an area surrounding or adjacent to substrate 22 to prevent surgery-related complications associated with the implantable medical device (such as to the "pocket" surrounding the device). For example, an anesthetic agent can be eluted into the surrounding bodily tissue, bodily fluid, or systemic fluid, to attenuate pain experienced at the implantation site. In another example, replacing the anesthetic agent with an anti-inflammatory agent can reduce the swelling and inflammation associated implantation of substrate 22. In yet another example, an antimicrobial agent can be provided at a rate of drug release sufficient to prevent or reduce colonization of substrate 22, the implantable medical device and/or the surgical implantation site by bacteria, for example, for at least the period following surgery necessary for initial healing of the surgical incision.

In some embodiments, the active pharmaceutical ingredient may be eluted for up to 30 days. In some embodiments, between about 40% and about 100% of the active pharmaceutical ingredient is released over a period of at least about 30 hours. In some embodiments, 60% and about 100% of the active pharmaceutical ingredient is released over a period of at least about 30 hours. In some embodiments, between about 65% and about 100% of the active pharmaceutical ingredient is released over a period of at least about 36 hours. In some embodiments, 80% and about 100% of the active pharmaceutical ingredient is released over a period of at least about 36 hours. In some embodiments, between about 60% and about 100% of the active pharmaceutical ingredient is released over a period of at least about 48 hours. In some embodiments, 80% and about 100% of the active pharmaceutical ingredient is released over a period of at least about 48 hours. In some embodiments, between about 60% and about 100% of the active pharmaceutical ingredient is released over a period of at least about 60 hours. In some embodiments, 80% and about 100% of the active pharmaceutical ingredient is released over a period of at least about 60 hours.

In some embodiments, substrate 22 includes a hydrophilic component, such as, for example, PEG and a crosslinking agent that is applied to substrate 22. The hydrophilic component and the crosslinking agent form a hydrogel that absorbs blood and reduces bleeding when in contact with blood or tissue fluid. In some embodiments, the hydrophilic component and the crosslinking agent are sprayed directly onto substrate 22. In some embodiments, the hydrophilic component and the crosslinking agent are provided in a polymer, such as, for example, one or more of the polymers discussed herein, and the polymer is applied directly onto substrate 22. In some embodiments, the hydrophilic component and the crosslinking agent are provided in a patch, such as, for example, the Veriset™ hemostatic patch available from Medtronic, Inc., and the patch is applied directly onto substrate 22. In some embodiments, the patch comprises a plurality of layers. For example, a first layer of the patch can include a hemostatic agent, such as, for example, oxidized regenerated cellulose and/or one or more of the hemostatic agents discussed herein. A second layer of the patch can include a crosslinking agent, such as, for example, trilysine and/or one or more of the crosslinking agents discussed herein. A third layer of the patch can include a hydrophilic agent, such as, for example, PEG and/or one or more of the hydrophilic agents discussed herein. The second layer of the patch is positioned between the first and third layers of the patch.

In some embodiments, the hydrophilic component comprises thermogelling hydrogels, PEG-PLGA copolymers, PEG-Poly(N-isopropyl acrylamide), Pluronic (PEO-PPO-PEO triblock), PEG-PCL polymers, PEG-based amphiphilic copolymers modified by anionic weak polyelectrolytes, (such as polyacrylic acid, polyglutamic acid) and polymers containing sulfonamide groups), PEG-based amphiphilic copolymers modified by cationic weak polyelectrolytes (such as poly (2-vinyl pyridine), Poly(beta-amino esters), poly (2-(dimethylamino)ethyl methacrylate), multiarm PEG derivatives such as those available from JenKem technology, multiarmed block and graft PLA copolymers with PEG, PEG with stereo complexed poly(lactide), acrylated polymers (such as Polyvinylalcohol, dextran, Polyvinylpyrollidone, chitosan, alginate, hyaluronic acid), and combinations thereof. In some embodiments, the crosslinking agent comprises one or more agents that induce polymerization of vinyl groups using various initiators, light or redox reactions, or by reactions such as Schiff base formation, Michael type additions, peptide ligation, clock chemistry of functional groups present; one or more agents that induce crosslinking by enzymatic reaction (transglutaminase mediated reaction between carboxamide and amine on proteins), stereo-complexation, metal chelation (alginates using calciumCal2), thermogelation, self-assembly (formation of super helices from protein chains) inclusion complexation (using cyclodextrin); and combinations thereof.

In some embodiments, implantable medical device 24 is not part of kit 20. In some embodiments, implantable medical device 24 is part of kit 20, as shown in FIG. 1. In embodiments wherein implantable medical device 24 is part of kit 20, it is envisioned that implantable medical device 24 may be packaged separately from substrate 22 or together with substrate 22. For example, in some embodiments, implantable medical device 24 may be packaged in a first container, such as, for example, package 26a shown in FIG. 5 and substrate 22 may be packaged in a second container, such as, for example, package 26b. Alternatively, implantable medical device 24 and substrate 22 may be packaged together in the same container, such as, for example, package 26a or package 26b. In some embodiments, at least one of package 26a and package 26b is sterilized.

In some embodiments, implantable medical device 24 is selected from the group consisting of neurostimulators, vascular devices such as grafts (e.g., abdominal aortic aneurysm grafts, etc.), stents, catheters (including arterial, intravenous, blood pressure, stent graft, etc.), valves (e.g., polymeric or carbon mechanical valves,), embolic protection filters (including distal protection devices), vena cava filters, aneurysm exclusion devices, artificial hearts, cardiac jackets, and heart assist devices (including left ventricle assist devices), implantable defibrillators, subcutaneous implantable defibrillators, implantable monitors, for example, implantable cardiac monitors, electrostimulation devices and leads (including pacemakers, lead adapters and lead connectors), implanted medical device power supplies, peripheral cardiovascular devices, atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters).

In some embodiments, implantable medical device 24 is selected from the group consisting of sutures of all types, anastomosis devices (including anastomotic closures), suture anchors, hemostatic barriers, screws, plates, dips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps. In some embodiments, implantable medical device 24 is selected from the group consisting of orthopedic devices such as joint implants, acetabular cups, patellar buttons, bone repair/augmentation devices, spinal devices (e.g., vertebral disks and the like), bone pins, cartilage repair devices, and artificial tendons. In some embodiments, implantable medical device 24 is selected from the group consisting of dental devices such as dental implants and dental fracture repair devices. In some embodiments, implantable medical device 24 is selected from the group consisting of drug delivery devices such as drug delivery pumps, implanted drug infusion tubes, drug infusion catheters, and intravitreal drug delivery devices. In some embodiments, implantable medical device 24 is selected from the group consisting of ophthalmic devices such as scleral buckles and sponges, glaucoma drain shunts and intraocular lenses.

In some embodiments, implantable medical device 24 is selected from the group consisting of urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices. In some embodiments, implantable medical device 24 is selected from the group consisting of synthetic prostheses such as breast prostheses and artificial organs (e.g., pancreas, liver, lungs, heart, etc.). In some embodiments, implantable medical device 24 is selected from the group consisting of respiratory devices including lung catheters. In some embodiments, implantable medical device 24 is selected from the group consisting of neurological devices such as neurostimulators, neurological catheters, neurovascular balloon catheters, neuro-aneurysm treatment coils, and neuropatches, splints, ear wicks, ear drainage tubes, tympanostomy vent tubes, otological strips, laryngectomy tubes, esophageal tubes, esophageal stents, laryngeal stents, salivary bypass tubes, and tracheostomy tubes. In some embodiments, implantable medical device 24 is selected from the group consisting of oncological implants and pain management implants.

Kit 20 includes an agent, such as, for example, a hemostatic agent 28. In some embodiments, hemostatic agent 28 is packaged in a container, such as, for example, a vial 30, as shown in FIG. 1. Hemostatic agent 28 is packaged separately from substrate 22 that is coated with the polymer including the active pharmaceutical agent. In some embodiments, hemostatic agent 28 is water soluble and is insoluble in organic solvents. In some embodiments, hemostatic agent 28 is water soluble and is denatured by organic solvents. In some embodiments, a solution comprising hemostatic agent 28 and an organic solvent is stored within vial 30. In some embodiments, a solution comprising hemostatic agent 28 and PEG is stored within vial 30. In some embodiments, a solution comprising hemostatic agent 28 is stored within vial 30 and kit 20 includes a vial similar to vial 30 containing PEG. This allows hemostatic agent 28 and PEG to be administered to a target area together such that the PEG forms a gel when it is introduced into the patient to prevent migration of hemostatic agent 28 within the patient, as discussed herein. In some embodiments, a powder comprising hemostatic agent 28 is stored within vial 30 and kit 20 includes a vial similar to vial 30 containing an organic solvent such that the organic solvent can be added to vial 30 at the time of surgery to reconstitute hemostatic agent 28.

Figure 5:
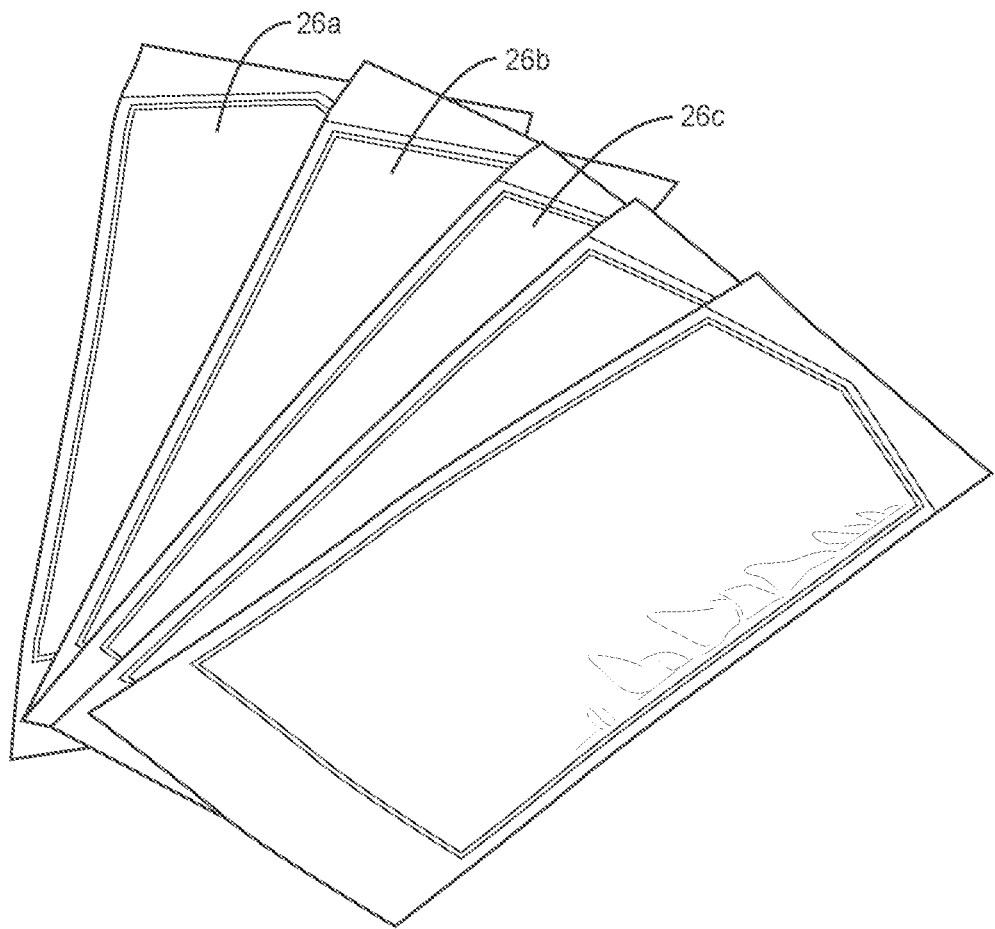
FIG. 5 is a perspective view of components of the kit shown in FIG. 1.

In some embodiments, implantable medical device 24 may be packaged in a first container, such as, for example, package 26a shown in FIG. 5, substrate 22 may be packaged in a second container, such as, for example, package 26b, and vial 30 may be packaged in a third container, such as, for example, package 26c. In some embodiments, implantable medical device 24 may be packaged in a first container, such as, for example, package 26a and substrate 22 and vial 30 may be packaged in a second container, such as, for example, package 26b or package 26c. In some embodiments, implantable medical device 24 and substrate 22 may be packaged in a first container, such as, for example, package 26a and vial 30 may be packaged in a second container, such as, for example, package 26b or package 26c. In some embodiments, vial 30 and substrate 22 may be packaged in a first container, such as, for example, package 26a and implantable medical device 24 may be packaged in a second container, such as, for example, package 26b or package 26c. In some embodiments, vial 30, implantable medical device 24, substrate 22 may be packaged together in the same container, such as, for example, package 26a, package 26b, or package 26c. In some embodiments, at least one of package 26a, package 26b and package 26c is sterilized.

Hemostatic agent 28 can include one more hemostatic agent, such as, for example, epinephrine, tranexamic acid, chitosan and oxidized regenerated cellulose. In some embodiments, hemostatic agent 28 can include one or more of Spongostan®, Surgifoam®, Avitene, thrombin and Ostene® in addition to or in place of the hemostatic agents discussed above. In some embodiments, hemostatic agent 28 can include one or more of protamine, norepinephrine, desmopressin, lysine analogs, collagen, gelatin, polysaccharide spheres, mineral zeolite, bovine thrombin, pooled human thrombin, recombinant thrombin, gelatin and thrombin, collagen and thrombin, cyanacrylate, fibrin glue, polyethylene glycol, and glutaraldehyde in addition to or in place of the hemostatic agents discussed above. In some embodiments, the lysine analog is tranexamic acid and has the formula:

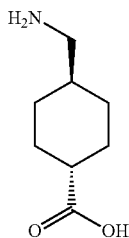 [SMILES: NC[C@H]1CC[C@H](C(=O)O)CC1]

In some embodiments, hemostatic agent 28 includes one or more pharmacologic hemostatic agent since pharmacologic hemostatic agents have been found to be desirable over mechanical hemostats for a variety of reasons. Ethnographic research has showed that physicians desire a hemostat that can provide an extended elution profile to reduce bleeding events for up to 7 days post operatively. Furthermore, there is a possible effect on handling and/or allergic reactions if mechanical hemostats, such as, for example, oxidized regenerated cellulose or chitosan were used.

In some embodiments, tranexamic acid is preferred for use as hemostatic agent 28. Tranexamic acid is a synthetic analog of the amino acid lysine with a molecular weight of 157 g/mol. Tranexamic acid is an antifibrinolytic agent that acts by binding to plasminogen and blocking the interaction of plasminogen with fibrin, therefore preventing the dissolution of a fibrin clot. In the presence of a wound, fibrinolysis occurs naturally when a lysine residue such as tissue plasminogen activator (tPA), binds to plasmin causing the clot to lyse (or break). Tranexamic acid blocks tPA and keeps the clot from breaking, thus preventing unwanted bleeding.

Prior to a damaged endothelium, tPA is inhibited in the blood by plasminogen activator inhibitor/type 1 (PAI-1). Once damage occurs, the tPA is released slowly into the blood, activating fibrinolysis. Excessive fibrinolysis results in a condition called hvperfibrinolysis, which requires intervention such as fibrinogen, plasma, transfusion or antifibrinolytic therapy, such as tranexamic acid.

Tranexamic acid has been used for over 40 years to reduce bleeding complications. Tranexamic acid is most commonly given systemically at doses of 10 mg/kg followed by infusion of 10 mg/kg/h. Since 2007, tranexamic acid has received widespread approval and clinical use as a hemostatic agent. Knowing that surgical trauma causes fibrinolysis in the area of the surgical wound itself, topical antifibrinolytic therapy is becoming more common to obtain and maintain hemostasis. Clinical trials with topical tranexamic acid use exist for cardiac surgery, CIED procedures, orthopedic surgery, spinal surgery, dental extraction and epistaxis, and breast mammoplasty.

To evaluate the efficacy of tranexamic acid, a non-GLP acute porcine study was conducted. Doses of 1 mg to 200 mg of tranexamic acid were used in an in vitro whole blood coagulation test, a hepatic biopsy test, and a subcutaneous ICD surgical procedure.

The in vitro whole blood coagulation test showed no activity for tranexamic acid up to 10 mg/ml. The maximum tranexamic acid concentration, 200 mg/5 ml, was a slightly higher dose than that used clinically in a CIED pocket if 50 cc is the assumed blood volume of interest Coagulation time was doubled with this higher dose.

The hepatic biopsy test had a volume of 0.016 ml when the biopsy hole was filled with blood. The minimum tranexamic acid dose evaluated was 2.5 mg, which is equivalent to 156 mg/ml. This concentration prevents blood from clotting quickly and these biopsies continued to bleed past the endpoint of 10 minutes. This phenomenon is likely due to the multiple bonding sites available to tranexamic acid in whole blood, and the fact that a biopsy does not induce fibrinolysis.

The subcutaneous surgical site test was conducted with an elevated ACT using heparin to induce hematoma. Surgical trauma similar to that of a CIEO implant was incurred in each pocket, but some subcutaneous pockets incurred more trauma than others due to anatomical location. The primary output monitored was accumulated blood as measured by pre-weighed gauze 3-hours post-operatively. With only one animal, and two pockets per treatment, the sample size was too low to show any significance between ICD only, ICD+ polymer, and ICD+polymer+tranexamic acid.

The non-GLP acute porcine study showed that in the dose range evaluated, tranexamic acid has a two-fold increase on clotting time and no effect on reducing bleeding on the hepatic biopsies. In the heparinized ICD pocket procedure, 3.5-22.8 grams of blood accumulated in a 3-hour period of time regardless of treatment. It appears that subcutaneous pockets in an anticoagulated porcine model would be a translatable model for evaluating efficacy of tranexamic acid because it has a relevant volume of accumulated blood and surgical trauma similar to that of a CIED procedure.

Based upon the non-GLP acute porcine study, tranexamic acid concentrations of 3.00 mg/L to 30 mg/L are effective in preventing fibrinolysis. As such, in some embodiments, hemostatic agent 28 is tranexamic acid and is provided in concentrations of about 3.00 mg/L to about 30 mg/L. However, it has been found that one tenth of the doses used in the non-GLP acute porcine study can be effective in reversing fibrinolysis. As such, in some embodiments, hemostatic agent 28 is tranexamic acid and is provided in concentrations of about 0.30 mg/L to about 3.0 mg/L for intravenous applications. In some embodiments, tranexamic acid is provided in concentrations of about 3.78 mg/L to about 30 mg/L for topical applications as well. However, in some embodiments, however, higher doses of tranexamic acid are used for topical applications to account for tranexamic acid being widely distributed throughout the extracellular and intracellular compartments when given preoperatively. Indeed, it has been found that tranexamic acid reaches plasma concentrations in 5-15 minutes. As such, in some embodiments, tranexamic acid is provided in doses of about 1.5 mg to about 150 mg. In some embodiments, hemostatic agent 28 includes a mixture or combination of the hemostatic agents discussed herein.

In some embodiments, hemostatic agent 28 includes one or more naturally occurring inhibitors of fibrinolysis. In some embodiments, the inhibitors of fibrinolysis are selected from agents that inhibit the activation of plasminogen and agents that act against plasmin directly Plasmin inhibitors include, for example, $\alpha_1$-Antitrypsin (mol. wt. 54000, mean concentration 290 (mg/100 ml), $\alpha_2$-Macroglobulin (mol. wt. 820000, mean concentration 260 (mg/100 ml), Inter-$\alpha_1$-inhibitor (mol. wt. 160000, mean concentration 50 (mg/100 ml), C1-inactivator (mol. wt. 104000, mean concentration 24 (mg/100 ml), and Antithrombin III (mol. wt. 65000, mean concentration 40 (mg/100 ml). In some embodiments, hemostatic agent 28 includes one or more inhibitors from blood platelets. In some embodiments, hemostatic agent 28 includes one or more endogenous inhibitors of fibrinolysis from other body fluids and tissues, such as, for example, urokinase inhibitors. In some embodiments, hemostatic agent 28 includes one or more inhibitors of proteolytic enzymes from animals (non-humans), such as, for example, human parasites and non-human parasites. In some embodiments, hemostatic agent 28 includes one or more inhibitors from bovine organs, bovine colostrum, guinea pig seminal vesicles, dog submandibular glands, leeches and/or snails. In some embodiments, hemostatic agent 28 includes Aprotinin, Iniprol, Trasylol and/or Contrykal. In some embodiments, hemostatic agent 28 includes one or more protease inhibitors from plants, such as, for example, trypsin inhibitors from soybeans, potatoes, peanuts and/or lima beans. In some embodiments, hemostatic agent 28 includes one or more agents discussed in Markward F. Naturally occurring inhibitors of fibrinolysis, In: Markwardt F, ed. Fibrinolytics and anti-fibrinolytics (Handbuch der experimentellen Pharmakologie, vow 46), Berlin: Springer, 1978: 487-509, which is expressly incorporated by reference herein, in its entirety.

In some embodiments, hemostatic agent 28 includes one or more synthetic inhibitors of fibrinolysis, such as, for example, ε-Aminocaproic acid (EACA), p-aminomethylbenzoic acid (PAMBA), trans-4-aminomethylcyclohexanecarboxylic acid-(1) (AMCA), 4-Aminobenzoic acid, 4-Aminocyclohexanecarboxylic acid-(1), cis/trans-4-Aminomethylcyclohexanecarboxylic acid-(1) (AMCA), 4-Aminoethylbenzoic acid, 4-Aminoethylcyclohexanecarboxyic acid-(1), 4-Aminophenylacetic acid, 4-aminocyclohexane-acetic acid, 4-Aminomethylphenyl acetic acid and/or 4-Aminomethylcyclohexane acetic acid. In some embodiments, hemostatic agent 28 includes derivatives of PAMBA, such as, for example, PAMBA methyl ester, PAMBA ethyl ester, PAMBA amide, 4-Aminomethylbenzene sulphonic acid, benzylamine, N-Acetyl-PAMBA, N-Dimethyl-PAMBA, Carbamyl-PAMBA, 4-Guanidinomethyl-benzoic acid, 4-Amidinobenzoic acid, 4-Guanidinobenzoic acid, 4-Toluic acid, 4-($\alpha$-Amino)-ethylbenzoic acid, 4-($\alpha$-Amino)-propylbenzoic acid, 2-Hydroxy-PAMBA, 3-Nitro-PAMBA and/or 3-Aminomethylbenzoic acid. In some embodiments, hemostatic agent 28 includes derivatives of benzylamine. In some embodiments, hemostatic agent 28 includes derivatives of lysine and/or other basic amino acids. In some embodiments, hemostatic agent 28 includes quaternary products of EACA, quaternary products of other ε-aminocarboxylic acids, primary aliphatic amines, lactams of carboxylic acids and/or lactones of carboxylic acids. In some embodiments, hemostatic agent 28 includes one or more agents discussed in Markward F. Synthetic inhibitors of fibrinolysis, In: Markwardt F, ed. Fibrinolytics and anti-fibrinolytics (Handbuch der experimentellen Pharmakologie, vol 46), Berlin: Springer, 1978: 511-77, which is expressly incorporated by reference herein, in its entirety. It is envisioned that hemostatic agent 28 can include one or more of any of the hemostatic agents discussed herein.

Hemostatic agent 28 is configured to be delivered to a target area to reduce or prevent bleeding within a patient, such as, for example, bleeding caused by a surgical procedure. By providing substrate 22 and hemostatic agent 28 separately, kit 20 allows hemostatic agent 28 to be administered before substrate 22 is implanted, at the same time that substrate 22 is implanted, or after substrate 22 is implanted. Providing substrate 22 and hemostatic agent 28 separately eliminates the need to develop a formulation of hemostatic agent in the polymer that coats substrate 22. That is, the type of hemostatic agent and the amount of hemostatic agent can be selected using hemostatic agent 28, rather than incorporating a hemostatic agent into substrate 22 and/or the polymer that coats substrate 22. Therefore, in some embodiments, kit 20 includes a plurality of containers similar to vial 30 wherein each container includes a different hemostatic agent, such as, for example, one or more of the hemostatic agents discussed herein. This allows a medical practitioner to select the hemostatic agent from kit 20 that is best suited for a particular application. In some embodiments, kit 20 includes a plurality of containers similar to vial 30 wherein each container includes the same hemostatic agent, such as, for example, one or more of the hemostatic agents discussed herein, wherein each container has a different amount or concentration of the hemostatic agent.

In some embodiments, kit 20 includes an absorbable substrate 32. In some embodiments, kit 20 includes a plurality of substrates 32. In some embodiments, substrates 32 are packaged in a container, such as, for example, a dispenser 34, as shown in FIG. 1. In some embodiments, dispenser 34 is configured to dispense one substrate 32 at a time. Substrates 32 are configured to absorb hemostatic agent 28. That is, substrates 32 can be soaked in a selected amount or selected concentration of hemostatic agent 28 until substrates 32 absorb hemostatic agent 28. In some embodiments, once at least one of substrates 32 is at least partially absorbs hemostatic agent 28, at least one of substrates 32 can be applied to substrate 22 such to allow the polymer that coats substrate 22 and/or substrate 22 itself to absorb hemostatic agent 28. Substrate 22 is implanted in the patient after substrate 22 and/or the polymer that coats substrate 22 absorbs hemostatic agent to administer hemostatic agent 28 to a target area within the patient. In some embodiments, substrate 32 is removed from substrate 22 before substrate 22 is implanted within the patient. In some embodiments, substrate 32 is coupled to substrate 22 when substrate 22 is implanted within the patient. In some embodiments, substrate 32 is coupled to substrate 22 after substrate 22 is implanted within the patient That is, substrate 32 is implanted in the patient after substrate 22 is implanted.

In some embodiments, substrate 32 comprises a planar single layer sheet. In some embodiments, substrate 32 comprises a sheet that includes oxidized regenerated cellulose Oxidized cellulose, Cellulose derivatives like carboxymethyl, hydroxypropyl, hydroxyethyl, Hyaluronic acid, Plant based polysaccharides, Gelatin, collagen, Chitosan, PVP, Polyacrylic acid, Copolymers of PEG and hydroxyacid polymers—such as polymers comprising lactic acid, glycolic acid, e-caprolactone, dioxanone, trimethylene carbonate, hydroxy alkanoates like hydroxybutyrate, Copolymers of PEG with tyrosine derived diphenols, including polyarylates, polycarbonates, polyiminocarbonates, polyurethanes, Extracellular matrices-plant, animal or human derived. In some embodiments, substrate 32 comprises paper pulps, wherein the pulps are selected from the group consisting of softwood, hardwood, fiber crops, and mineral fibers. In some embodiments, substrate 32 comprises a sheet of filter paper. In some embodiments, the filter paper is creped to improve porosity. In some embodiments, the filter paper is qualitative filter paper. The qualitative filter paper may be selected from the group consisting of grade 1 qualitative filter paper, grade 2 qualitative filter paper, grade 3 qualitative filter paper, grade 4 qualitative filter paper, and grade 602h qualitative filter paper. In some embodiments, the filter paper is quantitative filter paper.

In some embodiments, kit 20 includes a second hemostatic agent, such as, for example, a hemostatic agent 36. In some embodiments, hemostatic agent 36 is packaged in a container, such as, for example, a vial 38, as shown in FIG. 1. In some embodiments, hemostatic agent 36 is water soluble and is insoluble in organic solvents. In some embodiments, hemostatic agent 36 is water soluble and is denatured by organic solvents. Hemostatic agent 36 may include one or more of the hemostatic agents discussed herein, such as, for example, one or more of the hemostatic agents discussed herein that define hemostatic agent 28. In some embodiments, hemostatic agent 36 is different than hemostatic agent 28. In some embodiments, hemostatic agent 36 is the same as hemostatic agent 28. In some embodiments, a solution comprising hemostatic agent 36 and an organic solvent is stored within vial 38. In some embodiments, a powder comprising hemostatic agent 36 is stored within vial 38 and kit 20 includes a vial similar to vial 38 containing an organic solvent such that the organic solvent can be added to vial 38 at the time of surgery to reconstitute hemostatic agent 36.

In some embodiments, hemostatic agent 36 is configured to polymerize or gel upon introduction into a human body. In some embodiments, hemostatic agent 36 is configured to polymerize or gel by chelation with metal ions, chemical reactions, or light. In some embodiments, hemostatic agent 36 comprises PEG. In some embodiments, hemostatic agent 36 consists of PEG. Hemostatic agent 28 and hemostatic agent 36 to be administered to a target are together such that the PEG forms a gel when it is introduced in the patient to prevent migration of hemostatic agent 28 within the patient, as discussed herein. In some embodiments, the PEG is selected from the group consisting of PEG-200, PEG-300, PEG-400, PEG-600, PEG-1000, PEG-1450, PEG-3350, PEG-4000, PEG-6000, PEG-8000, PEG-20000, PEG-400-succinate, PEG-600-succinate, and PEG-1000-succinate. In some embodiments, the PEG is a blend of different PEGs, such as, for example, a blend of two or more of the PEGs discussed herein. In some embodiments, a powder comprising hemostatic agent 36 is stored within vial 38 and kit 20 includes a vial similar to vial 38 containing an organic solvent such that the organic solvent can be added to vial 38 at the time of surgery to reconstitute hemostatic agent 26.

In some embodiments, kit 20 may include one or a plurality of mesh substrates, such as, for example, substrates 22. It is contemplated that each of the mesh substrates can have a different configuration. In some embodiments, the mesh substrates can include different active pharmaceutical ingredients and/or different amounts of active pharmaceutical ingredients. In some embodiments, the mesh substrates can include different sizes and/or shapes, to accommodate different size implantable medical devices, for example. In some embodiments, kit 20 includes one or a plurality of medical devices, such as, for example, the implantable medical devices discussed herein. In some embodiments, kit 20 includes instructions for use.

In operation and use, substrate 22 is configured to be implanted at a target site in the body of a patient such that substrate 22 covers at least a portion of one or more implantable medical device 24, which is implanted at the target site. In some embodiments, substrate 22 is coupled to implantable medical device 24 before implantable medical device 24 is implanted at the target site. That is, implantable medical device 24 is implanted with substrate 22 coupled to implantable medical device 24 to implant implantable medical device 24 and substrate 22 simultaneously.

In some embodiments wherein hemostatic agent 28 is in a solution, substrate 22 may be soaked in hemostatic agent 28 before implantable medical device 24 and substrate 22 are implanted, such that the polymer that coats substrate 22 and/or substrate 22 itself absorb hemostatic agent 28. Implantable medical device 24 is then implanted with substrate 22 coupled to implantable medical device 24.

In some embodiments wherein kit 20 includes substrate(s) 32, at least one substrate 32 may be soaked with hemostatic agent 28 such that substrate(s) 32 absorb hemostatic agent 28. Substrate(s) 32 is/are then draped over substrate 22 such that the polymer that coats substrate 22 and/or substrate 22 itself absorb hemostatic agent 28 from substrate(s) 32. Implantable medical device 24 is then implanted with substrate 22 coupled to implantable medical device 24. In some embodiments, substrate(s) 32 is/are removed from substrate 22 before substrate 22 is coupled to implantable medical device 24. In some embodiments, substrate(s) 32 is/are coupled to substrate 22 when substrate 22 is coupled to implantable medical device 24. That is, substrate(s) 32 is/are implanted with substrate 22 such that substrate(s) 32 remain within the patient after the surgical procedure is complete.

In some embodiments wherein hemostatic agent 28 is in a solution, hemostatic agent may be administered to the target site before, during or after implantable medical device 24 and substrate 22 are implanted. For example, hemostatic agent 28 may be delivered to the target location before implantable medical device 24 is implanted with substrate 22 coupled to implantable medical device 24. Alternatively, hemostatic agent 28 may be delivered to the target location at the same time implantable medical device 24 is implanted with substrate 22 coupled to implantable medical device 24. Alternatively, hemostatic agent 28 may be delivered to the target location after implantable medical device 24 is implanted with substrate 22 coupled to implantable medical device 24. In some embodiments, hemostatic agent 28 is injected into the patient. In some embodiments, hemostatic agent 28 is injected into the patient such that hemostatic agent 28 comes into contact with substrate 22 and/or implantable medical device 24.

In some embodiments wherein kit 20 includes hemostatic agent 36, substrate 22 may be soaked in hemostatic agent 36 before implantable medical device 24 and substrate 22 are implanted, such that the polymer that coats substrate 22 and/or substrate 22 itself absorb hemostatic agent 36. Implantable medical device 24 is then implanted with substrate 22 coupled to implantable medical device 24. When hemostatic agent 36 is introduced into the patient, hemostatic agent 36 will cross-link to form a gel to prevent hemostatic agent 28 from migrating from the target area and/or reduce the amount that hemostatic agent 28 migrates from the target area. In some embodiments, substrate 22 may also be soaked in hemostatic agent 28 before implantable medical device 24 and substrate 22 are implanted, such that the polymer that coats substrate 22 and/or substrate 22 itself absorb hemostatic agent 28. In some embodiments, hemostatic agent 28 is added or otherwise combined with hemostatic agent 36 and substrate 22 is soaked in hemostatic agents 28, 36 before implantable medical device 24 and substrate 22 are implanted, such that the polymer that coats substrate 22 and/or substrate 22 itself absorbs hemostatic agents 28, 36. Implantable medical device 24 is then implanted with substrate 22 coupled to implantable medical device 24. In some embodiments, hemostatic agent 36 includes a cross-linking agent, such as, for example, one or more of the cross-linking agents discussed herein.

In some embodiments wherein kit 20 includes hemostatic agent 36, hemostatic agent 28 is added or otherwise combined with hemostatic agent 36. Implantable medical device 24 is implanted with substrate 22 coupled to implantable medical device 24. Hemostatic agents 28, 36 are injected together to deliver hemostatic agents 28, 36 to the target area. In some embodiments, hemostatic agents 28, 36 are injected before implantable medical device 24 is implanted with substrate 22 coupled to implantable medical device 24. In some embodiments, hemostatic agents 28, 36 are injected after implantable medical device 24 is implanted with substrate 22 coupled to implantable medical device 24. In some embodiments, hemostatic agents 28, 36 are injected at the same time implantable medical device 24 is implanted with substrate 22 coupled to implantable medical device 24.

In some embodiments wherein kit 20 includes hemostatic agent 36, hemostatic agents 28, 36 are each injected into the patient to deliver hemostatic agents 28, 36 to the target area. In some embodiments, hemostatic agent 28 is injected into the patient before hemostatic agent 36 is injected into the patient. In some embodiments, hemostatic agent 28 is injected into the patient after hemostatic agent 36 is injected into the patient. In some embodiments, hemostatic agents 28, 36 are injected into the patient simultaneously using different delivery devices, such as, for example, different syringes. In some embodiments, at least one of hemostatic agents 28, 36 is injected into the patient before implantable medical device 24 is implanted with substrate 22 coupled to implantable medical device 24. In some embodiments, at least one of hemostatic agents 28, 36 is injected into the patient after implantable medical device 24 is implanted with substrate 22 coupled to implantable medical device 24. In some embodiments, at least one of hemostatic agents 28, 36 is injected into the patient at the same time implantable medical device 24 is implanted with substrate 22 coupled to implantable medical device 24.

In some embodiments wherein kit 20 includes substrate(s) 32 and hemostatic agent 36, substrate(s) 32 may be soaked in hemostatic agent 36 before implantable medical device 24 and substrate 22 are implanted. Substrate(s) 32 is/are then draped over substrate 22 such that the polymer that coats substrate 22 and/or substrate 22 itself absorb hemostatic agent 36. Implantable medical device 24 is then implanted with substrate 22 coupled to implantable medical device 24. When hemostatic agent 36 is introduced into the patient, hemostatic agent 36 will cross-link to form a gel to prevent hemostatic agent 28 from migrating from the target area and/or reduce the amount that hemostatic agent 28 migrates from the target area. In some embodiments, substrate(s) 32 may also be soaked in hemostatic agent 28 before implantable medical device 24 and substrate 22 are implanted. Substrate(s) 32 is/are then draped over substrate 22 such that the polymer that coats substrate 22 and/or substrate 22 itself absorb hemostatic agent 28. In some embodiments, hemostatic agent 28 is added or otherwise combined with hemostatic agent 36 and substrate(s) 32 is/are soaked in hemostatic agents 28, 36 before implantable medical device 24 and substrate 22 are implanted, such that the polymer that coats substrate 22 and/or substrate 22 itself absorb hemostatic agents 28, 36. Implantable medical device 24 is then implanted with substrate 22 coupled to implantable medical device 24. In some embodiments, substrate(s) 32 is/are removed from substrate 22 before substrate 22 is coupled to implantable medical device 24. In some embodiments, substrate(s) 32 is/are coupled to substrate 22 when substrate 22 is coupled to implantable medical device 24. That is, substrate(s) 32 is/are implanted with substrate 22 such that substrate(s) 32 remain within the patient after the surgical procedure is complete.

In some embodiments, substrate 22 is coupled to implantable medical device 24 after implantable medical device 24 is implanted at the target site. That is, implantable medical device 24 is implanted by itself. Substrate 22 is then coupled to implantable medical device 24.

In some embodiments wherein hemostatic agent 28 is in a solution, substrate 22 may be soaked in hemostatic agent 28 before substrate 22 is coupled to implantable medical device, such that the polymer that coats substrate 22 and/or substrate 22 itself absorb hemostatic agent 28. Substrate 22 is then coupled to implantable medical device 24, which was implanted previously.

In some embodiments wherein kit 20 includes substrate(s) 32, at least one substrate 32 may be soaked with hemostatic agent 28 such that substrate(s) 32 absorb hemostatic agent 28. Substrate(s) 32 is/are then draped over substrate 22 such that the polymer that coats substrate 22 and/or substrate 22 itself absorb hemostatic agent 28 from substrate(s) 32. Substrate 22 is then coupled to implantable medical device 24, which was implanted previously. In some embodiments, substrate(s) 32 is/are removed from substrate 22 before substrate 22 is coupled to implantable medical device 24. In some embodiments, substrate(s) 32 is/are coupled to substrate 22 when substrate 22 is coupled to implantable medical device 24. That is, substrate(s) 32 is/are implanted with substrate 22 such that substrate(s) 32 remain within the patient after the surgical procedure is complete. In embodiments wherein hemostatic agent 28 and/or hemostatic agent 36 is/are injected into the patient, at least one of hemostatic agents 28, 36 may be provided as a solution in kit 20. In embodiments wherein hemostatic agent 28 and/or hemostatic agent 36 is/are injected into the patient, at least one of hemostatic agents 28, 36 may be provided as powder and kit 20 can include a liquid component, such as, for example, a non-organic solvent that may be added to hemostatic agent 28 and/or hemostatic agent 36 to reconstitute hemostatic agent 28 and/or hemostatic agent 36.

In some embodiments wherein hemostatic agent 28 is in a solution, hemostatic agent 28 may be administered to the target site after implantable medical device 24 and substrate 22 are implanted. That is, substrate 22 is coupled to implantable medical device 24 after implantable medical device 24 is implanted. Hemostatic agent 28 may then be delivered to the target site and/or an area adjacent to the target site after substrate 22 is coupled to implantable medical device 24. In some embodiments, hemostatic agent 28 is injected into the patient. In some embodiments, hemostatic agent 28 is injected into the patient such that hemostatic agent 28 comes into contact with substrate 22 and/or implantable medical device 24.

In some embodiments wherein kit 20 includes hemostatic agent 36, substrate 22 may be soaked in hemostatic agent 36 before implantable medical device 24 and substrate 22 are implanted, such that the polymer that coats substrate 22 and/or substrate 22 itself absorb hemostatic agent 36. Implantable medical device 24 is then implanted. Substrate 22 is then implanted such that substrate 22 covers at least a portion of implantable medical device 24, which was implanted before substrate 22 was implanted. When hemostatic agent 36 is introduced into the patient, hemostatic agent 36 will cross-link to form a gel to prevent hemostatic agent 28 from migrating from the target area and/or reduce the amount that hemostatic agent 28 migrates from the target area. In some embodiments, substrate 22 may also be soaked in hemostatic agent 28 before implantable medical device 24 is implanted, such that the polymer that coats substrate 22 and/or substrate 22 itself absorb hemostatic agent 28. In some embodiments, hemostatic agent 28 is added or otherwise combined with hemostatic agent 36 and substrate 22 is soaked in hemostatic agents 28, 36 before substrate 22 is implanted, such that the polymer that coats substrate 22 and/or substrate 22 itself absorb hemostatic agents 28, 36. Substrate 22 is then implanted such that substrate 22 covers at least a portion of implantable medical device 24, which was implanted before substrate 22 was implanted.

In some embodiments wherein kit 20 includes hemostatic agent 36, hemostatic agent 28 is added or otherwise combined with hemostatic agent 36. Substrate 22 is then implanted such that substrate 22 covers at least a portion of implantable medical device 24, which was implanted before substrate 22 was implanted. Hemostatic agents 28, 36 are injected together to deliver hemostatic agents 28, 36 to the target area. In some embodiments, hemostatic agents 28, 36 are injected into the patient before implantable medical device 24 and substrate 22 are implanted. In some embodiments, hemostatic agents 28, 36 are injected into the patient before implantable medical device 24 is implanted into the patient. In some embodiments, hemostatic agents 28, 36 are injected into the patient after implantable medical device 24 is implanted, but before substrate 22 is implanted. In some embodiments, hemostatic agents 28, 36 are injected into the patient at the same time implantable medical device 24 is implanted. In some embodiments, hemostatic agents 28, 36 are injected into the patient at the same time substrate 22 is implanted. In some embodiments, hemostatic agents 28, 36 are injected into the patient after substrate 22 is implanted.

In some embodiments wherein kit 20 includes hemostatic agent 36, hemostatic agents 28, 36 are each injected into the patient to deliver hemostatic agents 28, 36 to the target area. In some embodiments, hemostatic agent 28 is injected into the patient before hemostatic agent 36 is injected into the patient. In some embodiments, hemostatic agent 28 is injected into the patient after hemostatic agent 36 is injected into the patient. In some embodiments, hemostatic agents 28, 36 are injected into the patient simultaneously using different delivery devices, such as, for example, different syringes. In some embodiments, at least one of hemostatic agents 28, 36 is/are injected into the patient before implantable medical device 24 is implanted into the patient. In some embodiments, at least one of hemostatic agents 28, 36 is/are injected into the patient after implantable medical device 24 is implanted, but before substrate 22 is implanted. In some embodiments, at least one of hemostatic agents 28, 36 is/are injected into the patient at the same time implantable medical device 24 is implanted. In some embodiments, at least one of hemostatic agents 28, 36 is/are injected into the patient at the same time substrate 22 is implanted. In some embodiments, at least one of hemostatic agents 28, 36 is/are injected into the patient after substrate 22 is implanted.

In some embodiments wherein kit 20 includes substrate(s) 32 and hemostatic agent 36, substrate(s) 32 may be soaked in hemostatic agent 36 before implantable medical device 24 and/or substrate 22 are implanted. Substrate(s) 32 is/are then draped over substrate 22 such that the polymer that coats substrate 22 and/or substrate 22 itself absorb hemostatic agent 36. Substrate 22 is then implanted such that substrate 22 covers at least a portion of implantable medical device 24, which was implanted before substrate 22 was implanted. When hemostatic agent 36 is introduced into the patient, hemostatic agent 36 will cross-link to form a gel to prevent hemostatic agent 28 from migrating from the target area and/or reduce the amount that hemostatic agent 28 migrates from the target area. In some embodiments, substrate(s) 32 may also be soaked in hemostatic agent 28 before substrate 22 is implanted. Substrate(s) 32 is/are then draped over substrate 22 such that the polymer that coats substrate 22 and/or substrate 22 itself absorbs hemostatic agent 28. In some embodiments, hemostatic agent 28 is added or otherwise combined with hemostatic agent 36 and substrate(s) 32 is/are soaked in hemostatic agents 28, 36 before substrate 22 is implanted, such that the polymer that coats substrate 22 and/or substrate 22 itself absorb hemostatic agents 28, 36. Substrate 22 is then implanted such that substrate 22 covers at least a portion of implantable medical device 24, which was implanted before substrate 22 was implanted. In some embodiments, substrate(s) 32 is/are removed from substrate 22 before substrate 22 is implanted. In some embodiments, substrate(s) 32 is/are coupled to substrate 22 when substrate 22 is implanted. That is, substrate(s) 32 is/are implanted with substrate 22 such that substrate(s) 32 remain within the patient after the surgical procedure is complete.

Hemostatic agent 28 acts to reduce or prevent bleeding within the patient. In some embodiments, the polymer that coats substrate 22 releases an active pharmaceutical agent, such as, for example, one or more of the active pharmaceutical ingredients discussed herein to prevent, mitigate, or treat a condition within the patient, such as, for example, a bacterial infection.

In some embodiments, implantable medical device 24 is removed from the patient after the treatment is completed. In some embodiments, substrate 22 remains implanted within the patient after implantable medical device 24 is removed. In some embodiments, substrate 22 is removed from the patient after implantable medical device 24 is removed. To remove substrate 22, tissue that is ingrown within substrate 22 can be cut or otherwise detached from substrate 22. In some embodiments, a portion of substrate 22 may not be removable from the tissue and will remain implanted within the patient.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A kit comprising:
a substrate comprising collagen;
a tyrosine-derived polyesteramide polymer that that at least partially coats the substrate, the tyrosine-derived polyesteramide polymer including a combination of minocycline and rifampin; and
a hemostatic agent,
wherein the hemostatic agent is tranexamic acid, and
wherein the substrate is disposed in a first package and the hemostatic agent is disposed in a second package that is separate from the first package.

2. The kit recited in claim 1, wherein the packages are sterile.

3. The kit recited in claim 1, wherein the substrate consists of collagen.

4. The kit recited in claim 1, wherein the hemostatic agent is provided in a solution.

5. The kit recited in claim 1, wherein the hemostatic agent is provided in a suspension.

6. The kit recited in claim 1, wherein the substrate is a sheet.

7. The kit recited in claim 6, wherein the sheet has a thickness between about 0.0001 inches and about 0.1 inches.

8. A surgical method comprising:
providing a kit comprising:
a substrate comprising collagen,
a tyrosine-derived polyesteramide polymer that that at least partially coats the substrate, the tyrosine-derived polyesteramide polymer including a combination of minocycline and rifampin, and
a solution comprising tranexamic acid,
wherein the substrate is disposed in a first package and the solution is disposed in a second package that is separate from the first package;
removing the substrate from the first package;
soaking the substrate in the solution; and
implanting the substrate in a patient after the substrate is soaked in the solution.

9. The surgical method recited in claim 8 wherein the substrate consists of collagen prior to being soaked in the solution.

10. The surgical method recited in claim 8, further comprising coupling an implantable medical device to the substrate after soaking the substrate in the solution and before implanting the substrate in the patient.

11. A kit comprising:
a substrate consisting of collagen, the substrate being a sheet having a thickness between about 0.0001 inches and about 0.1 inches;
a tyrosine-derived polyesteramide polymer that that at least partially coats the substrate, the tyrosine-derived polyesteramide polymer including a combination of minocycline and rifampin; and
tranexamic acid,
wherein the substrate and the tyrosine-derived polyesteramide polymer are disposed in a first sterile package and the tranexamic acid comprises a solution or suspension that is disposed in a second sterile package that is separate from the first package.

12. The kit recited in claim 1, wherein the substrate is coated with a single layer of the polymer.

13. The kit recited in claim 1, wherein the substrate is coated with multiple layers of the polymer.

14. The kit recited in claim 1, wherein the substrate is a mesh.

15. The kit recited in claim 1, wherein the substrate includes a pocket configured for disposal of an implantable medical device.

16. The kit recited in claim 1, further comprising an implantable medical device configured for disposal in a pocket of the substrate.

17. The kit recited in claim 1, further comprising a second hemostatic agent.

18. The kit recited in claim 17, wherein the second hemostatic agent is disposed in a third package that is separate from the first package and the second package.

19. The kit recited in claim 17, wherein the second hemostatic agent is selected from the group consisting of epinephrine, chitosan, oxidized regenerated cellulose, thrombin, protamine, norepinephrine, desmopressin, lysine analogs, collagen, gelatin, polysaccharide spheres, mineral zeolite, calcium salt, bovine thrombin, pooled human thrombin, recombinant thrombin, gelatin and thrombin, collagen and thrombin, cyanacrylate, fibrin glue, polyethylene glycol, peptide, and glutaraldehyde.

* * * * *